US005639746A

United States Patent [19]
Yelm

[11] Patent Number: 5,639,746
[45] Date of Patent: Jun. 17, 1997

[54] HYDROXAMIC ACID-CONTAINING INHIBITORS OF MATRIX METALLOPROTEASES

[75] Inventor: Kenneth Edward Yelm, Fairfield, Ohio

[73] Assignee: The Procter & Gamble Company, Cincinnati, Ohio

[21] Appl. No.: 366,062

[22] Filed: Dec. 29, 1994

[51] Int. Cl.$^6$ .................... A61K 31/215; C07D 207/00; C07C 229/00

[52] U.S. Cl. .................... 514/210; 514/212; 514/277; 514/359; 514/507; 546/341; 548/535; 560/41; 560/49; 562/623

[58] Field of Search .................... 562/623; 560/41, 560/169; 514/507, 210, 212, 277, 359; 548/535; 546/341

[56] References Cited

U.S. PATENT DOCUMENTS

| | | | |
|---|---|---|---|
| 4,743,587 | 5/1988 | Dickens et al. | 514/575 |
| 4,771,038 | 9/1988 | Wolanin et al. | 514/18 |
| 4,918,105 | 4/1990 | Cartwright et al. | 514/575 |
| 4,996,358 | 2/1991 | Handa et al. | 562/621 |
| 5,183,900 | 2/1993 | Galardy et al. | 560/42 |
| 5,189,178 | 2/1993 | Galardy et al. | 548/495 |
| 5,300,674 | 4/1994 | Crimmin et al. | 560/42 |
| 5,310,763 | 5/1994 | Campion et al. | 514/575 |

FOREIGN PATENT DOCUMENTS

| | | | |
|---|---|---|---|
| 0 231 081 | 8/1987 | European Pat. Off. | C07K 5/06 |
| 0 258 616 A1 | 3/1988 | European Pat. Off. | A61K 49/00 |
| 0 337 348 | 10/1989 | European Pat. Off. | C07C 83/10 |
| 450-355-A | 4/1990 | European Pat. Off. | A01N 43/10 |
| 0 498 665 A1 | 8/1992 | European Pat. Off. | C07C 259/06 |
| 0 518 426 A1 | 12/1992 | European Pat. Off. | C07D 495/06 |
| 0 575 844 A2 | 12/1993 | European Pat. Off. | C07C 259/06 |
| 4127842A1 | 2/1993 | Germany | C07D 333/24 |
| 04217950-A | 8/1992 | Japan | C07C 259/06 |
| 2 268 934 | 1/1994 | United Kingdom | C07C 259/06 |
| 2 279 345 | 1/1995 | United Kingdom | C07C 235/82 |
| 91/02716 | 3/1991 | WIPO | C07C 259/06 |
| 91/08737 | 6/1991 | WIPO | A61K 31/16 |
| 92/09563 | 6/1992 | WIPO | C07C 259/00 |
| 92/17460 | 10/1992 | WIPO | C07D 245/02 |
| 93/00082 | 1/1993 | WIPO | A61K 31/16 |
| 93/09090 | 5/1993 | WIPO | C07C 259/06 |
| 93/13056 | 7/1993 | WIPO | A61K 31/16 |
| 93/20047 | 10/1993 | WIPO | C07C 317/44 |
| 93/21942 | 11/1993 | WIPO | A61K 37/02 |
| 94/10990 | 5/1994 | WIPO | A61K 31/16 |

OTHER PUBLICATIONS

Turbanti, L; Cerbai, G; Di Bugno, C; Giorgi, R.; Garzelli, G; Criscuoli, M, eta al. "1,2-Cyclomethylenecarboxylic Monoamide Hydroxamic Derivatives. A Novel Class of Non-Amino Acid Angiotensin Converting Enzyme Inhibitors", J. Med. Chem., vol. 36, pp. 699–707 (1993).

Johnson, W.H., N.A. Roberts and N. Borkakoti, "Collagenase Inhibitors: Their Design and Potential Therapeutic Use", J. Enzyme Inhibition, vol. 2, pp. 1–22, (No Month Identified 1987).

Odake, Sh., T. Okayama, M. Obata, T. Morikawa, S. Hattori, H. Hori and Y. Nagai, "Vertebrate Collagenase Inhibitor. II. Tetrapeptidyl Hydroxamic Acids", Chem. Pharm. Bull., vol. 39, No. 6, pp. 1489–1494 (Jun. 1991).

Turbanti, et al., J. Med Chem., vol. 36, No. 6, pp. 699–707 Mar. 19, 1993.

*Primary Examiner*—Joseph Conrad
*Attorney, Agent, or Firm*—Carl J. Roof; Richard A. Hake; Karen F. Clark

[57] ABSTRACT

The invention provides hydroxamic acid-containing compounds which are useful as inhibitors of matrix metalloproteases and which are effective in treating conditions associated with excess activity of these enzymes. In particular, the present invention relates to a compound having a structure according to Formula I

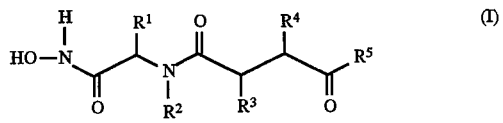

wherein
(A) $R^1$, $R^2$, $R^3$, $R^4$ and $R^5$ are independently selected from various substituents; and
(B) where $R^3$ and $R^4$ or $R^4$ and $R^5$ may together comprise a cyclic moiety; or a pharmaceutically-acceptable salt, biohydrolyzable amide or biohydrolyzable ester thereof.

In other aspects, the invention is directed to pharmaceutical compositions containing the compounds of Formula (I), and to methods of treating diseases characterized by matrix metalloprotease activity using these compounds or the pharmaceutical compositions containing them.

16 Claims, No Drawings

HYDROXAMIC ACID-CONTAINING INHIBITORS OF MATRIX METALLOPROTEASES

TECHNICAL FIELD

This invention is directed to compounds which are useful in treating diseases associated with excess and/or unwanted matrix metalloprotease activity, particularly stromelysin activity. More specifically, the invention is directed to hydroxamic acid-containing compounds.

BACKGROUND OF THE INVENTION

A number of enzymes effect the breakdown of structural proteins and are structurally related metalloproteases. These include human skin fibroblast collagenase, human skin fibroblast gelatinase, human sputum collagenase and gelatinase, and human stromelysin. These are zinc-containing metalloprotease enzymes, as are the angiotensin-converting enzymes and the enkephalinases. Stromelysin and related enzymes are important in mediating the symptomology of a number of diseases, including rheumatoid arthritis (Mullins, D. E., et al., Biochim Biophys Acta (1983) 695: 117–214); osteoarthritis (Henderson, B., et al., Drugs of the Future (1990) 15: 495–508); the metastasis of tumor cells (ibid, Broadhurst, M. J., et al., European Patent Application 276,436 (published 1987), Reich, R., et al., 48 Cancer Res 3307–3312 (1988); and various ulcerated conditions. Ulcerative conditions can result in the cornea as the result of alkali burns or as a result of infection by Pseudomonas aeruginosa, Acanthamoeba, Herpes simplex and vaccinia viruses.

Other conditions characterized by unwanted matrix metalloprotease activity include periodontal disease, epidermolysis bullosa and scleritis. In view of the involvement of matrix metalloproteases in a number of disease conditions, attempts have been made to prepare inhibitors to these enzymes. A number of such inhibitors are disclosed in the literature. Examples include U.S. Pat. No. 4,771,038, issued Sep. 13, 1988 to Wolanin, et al.; U.S. Pat. No. 4,743,587, issued May 10, 1988 to Dickens, et al., European Patent Publication Number 575,844, published Dec. 29, 1993 by Broadhurst, et al.; International Patent Publication No. WO 93/09090, published May 13, 1993 by Isomura, et al.; European Patent Publication Number 498,665, published Aug. 12, 1992 by Beckett, et al.; and U.S. Pat. No. 5,183,900, issued Feb. 2, 1993 to Galardy.

It is well known in the art that inhibitors of matrix metalloproteases are useful in treating diseases caused, at least in part, by breakdown of structural proteins. Though many inhibitors have been prepared, there is a continuing need for compounds useful in treating such diseases. The compounds of the present invention add to the repertoire of agents available for the treatment of conditions and diseases which are characterized by unwanted activity by the class of proteins which destroy structural proteins.

SUMMARY OF THE INVENTION

The invention provides compounds which are useful as inhibitors of matrix metalloproteases and which are effective in treating conditions characterized by excess activity of these enzymes. Further, unlike the prior art compounds, these compounds have reduced peptidic character, which may allow for improved bioavailability and stability. This improvement is important, as the peptidic nature of known inhibitors typically results in limited bioavailability because of proteolysis.

In particular, the present invention relates to a compound having a structure according to Formula I

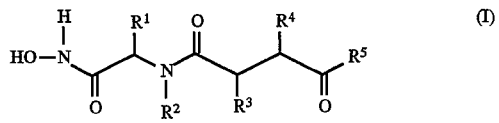

wherein
(A)
(1) $R^1$ is hydrogen; alkyl; heteroalkyl; alkenyl; benzyl; a heterocyclic ring; a carbocyclic ring; alkoxy; carbocycle-alkyl; heterocycle-alkyl; carbocycle-heteroalkyl; heterocycle-heteroalkyl; carbocycle-thio; or heterocycle-thio;
(2) $R^2$ is hydrogen; alkyl; alkenyl; alkynyl; a heterocyclic ring; a carbocyclic ring; carbocycle-alkyl; heterocycle-alkyl; or carbocycle-heteroalkyl;
(3) $R^3$ is hydrogen; alkyl; a carbocyclic ring; or a heterocyclic ring;
(4) $R^4$ is alkyl; heteroalkyl; alkylamino; acylamino; carboxyalkyl; aminoalkyl; a carbocyclic ring; a heterocyclic ring; heterocycle-heteroalkyl; heterocycle-alkyl; or a moiety capable of bearing a charge; and
(5) $R^5$ is
   (a) —O—$R_6$; where $R^6$ is hydrogen, alkyl, or benzyl;
   (b) —N($R_9$)CH($R_{10}$)($R_{11}$), where
      (i) $R^9$ is hydrogen or alkyl; and
      (ii) $R^{10}$ and $R^{11}$ are, independently, hydrogen, alkyl, arylalkyl, alkoxyacyl, or aminoacyl; or
      (iii) $R^9$ and $R^{10}$, together with the nitrogen and carbon atoms to which they are bonded, comprise a 4–9 atom monocyclic heterocyclic ring;
   (c) an amino acid or a peptide having 2 or 3 amino acids, wherein said amino acid or said peptide is bonded to Formula (I) via its amino group;
   (d) alkyl;
   (e) alkenyl;
   (f) carbocycle-alkyl; or
   (g) carbocycle-alkenyl;
(B) and where
(1) $R^3$ and $R^4$ may together comprise a 3–9 atom monocyclic carbocyclic ring; a 7–17 atom polycyclic carbocyclic ring; a 4–9 atom monocyclic heterocyclic ring; or a 7–17 atom polycyclic heterocyclic ring; or
(2) $R^4$ and $R^5$ may together comprise a 3–13 atom monocyclic carbocyclic ring; a 7–17 atom polycyclic carbocyclic ring; a 4–9 atom monocyclic heterocyclic ring; or a 7–17 atom polycyclic heterocyclic ring;
or a pharmaceutically-acceptable salt, biohydrolyzable amide or biohydrolyzable ester thereof.

These compounds have the ability to inhibit at least one mammalian matrix metalloprotease. Accordingly, in other aspects, the invention is directed to pharmaceutical compositions containing the compounds of Formula (I), and to methods of treating diseases characterized by matrix metalloprotease activity using these compounds or the pharmaceutical compositions containing them.

Matrix metalloproteases at a particularly undesired location can be targeted by conjugating the compounds of the invention to a targeting ligand specific for a marker at that location such as an antibody or fragment thereof or a receptor ligand.

The invention is also directed to various other processes which take advantage of the unique properties of these compounds. Thus, in another aspect, the invention is directed to the compounds of Formula (I) conjugated to solid supports. These conjugates can be used as affinity reagents for the purification of a desired matrix metalloprotease.

In another aspect, the invention is directed to the compounds of Formula (I) conjugated to label. As the compounds of the invention bind to at least one matrix metalloprotease, the label can be used to detect the presence of relatively high levels of matrix metalloprotease in vivo or in vitro cell culture.

In addition, the compounds of Formula (I) can be conjugated to carries which permit the use of these compounds in immunization protocols to prepare antibodies specifically immunoreactive with the compounds of the invention. These antibodies are then useful both in therapy and in monitoring the dosage of the inhibitors.

DETAILED DESCRIPTION

The compounds of the present invention are inhibitors of mammalian matrix metalloproteases. These compounds have a structure according to Formula I

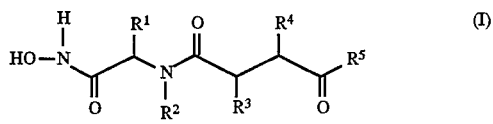

wherein (A)

(1) $R^1$ is hydrogen; alkyl; heteroalkyl; alkenyl; benzyl; a heterocyclic ring; a carbocyclic ring; alkoxy; carbocycle-alkyl; heterocycle-alkyl; carbocycle-heteroalkyl; heterocycle-heteroalkyl; carbocycle-thio; or heterocycle-thio; (preferably hydrogen, alkyl or carbocycle-alkyl; more preferably hydrogen, methyl, ethyl, isopropyl or 2-phenylethyl)

(2) $R^2$ is hydrogen; alkyl; alkenyl; alkynyl; a heterocyclic ring; a carbocyclic ring; carbocycle-alkyl; heterocycle-alkyl; or carbocycle-heteroalkyl (preferably $C_4$–$C_{10}$ alkyl, $C_4$–$C_{10}$ alkenyl, or carbocycle-alkyl; more preferably decyl, 2-methylpropyl, 2-phenylethyl, or 3-phenylpropyl)

(3) $R^3$ is hydrogen; alkyl; a carbocyclic ring; or a heterocyclic ring; (preferably hydrogen or alkyl, more preferably hydrogen, methyl or ethyl; most preferably hydrogen)

(4) $R^4$ is alkyl; heteroalkyl; alkylamino; acylamino; carboxyalkyl; aminoalkyl; a carbocyclic ring; a heterocyclic ring; heterocycle-heteroalkyl; heterocycle-alkyl; or a moiety capable of bearing a charge; (preferably 2-methylpropyl, carboxymethyl, 2-carboxyethyl, 4-aminobutyl, 2-phenylethyl, 3-phenylpropyl, benzyl, or 3-guanidinopropyl) and (5) $R^5$ is (a) —O—$R^6$; where $R^6$ is hydrogen, alkyl, or benzyl;

(b) (preferably) —N($R^9$)CH($R^{10}$)($R^{11}$), where
 (i) $R^9$ is hydrogen or alkyl; and
 (ii) $R^{10}$ and $R^{11}$ are, independently, hydrogen, alkyl, arylalkyl, alkoxyacyl, or aminoacyl; (preferably one of $R^{10}$ or $R^{11}$ is hydrogen) or
 (iii) $R^9$ and $R^{10}$, together with the nitrogen and carbon atoms to which they are bonded, comprise a 4–9 atom monocyclic heterocyclic ring;

(c) an amino acid or a peptide having 2 or 3 amino acids, wherein said amino acid or said peptide is bonded to Formula (I) via its amino group;

(d) alkyl;

(e) alkenyl;

(f) carbocycle-alkyl; or (g) carbocycle-alkenyl;

(B) and where (1) $R^3$ and $R^4$ may together comprise a 3–9 atom monocyclic carbocyclic ring; a 7–17 atom polycyclic carbocyclic ring; a 4–9 atom monocyclic heterocyclic ring; or a 7–17 atom polycyclic heterocyclic ring; (preferably a saturated monocyclic or polycyclic carbocyelic ring, more preferably a saturated moncocyclic carbocyclic ring) or (2) $R^4$ and $R^5$ may together comprise a 3–13 atom monocyclic carbocyclic ring; a 7–17 atom polycyclic carbocyclic ring; a 4–9 atom monocyclic heterocyclic ring; or a 7–17 atom polycyclic heterocyclic ring;

or a pharmaceutically-acceptable salt, biohydrolyzable amide or biohydrolyzable ester thereof.

Preferred compounds of Formula (I) are those where none of $R^3$, $R^4$, and $R^5$ combine to form a ring; and those where only $R^3$ and $R^4$ together form a ring. Most preferred is where none of $R^3$, $R^4$, and $R^5$ combine to form a ring.

Examples of preferred $R^5$ groups include, but are not limited to,

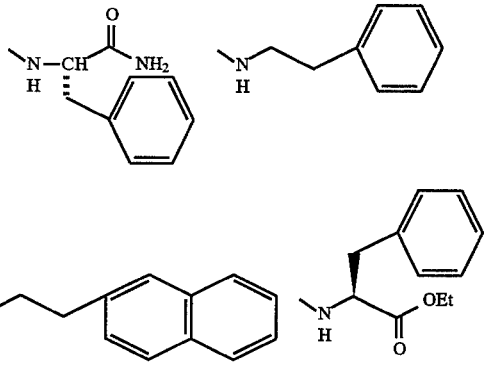

Definitions and Usage of Terms:

The following is a list of definitions for terms used herein.

"Acyl" or "carbonyl" is a radical formed by removal of the hydroxy from a carboxylic acid (i.e., R—C(=O)—). Preferred acyl groups include (for example) acetyl, formyl, and propionyl.

"Acyloxy" is an oxygen radical having an acyl substituent (i.e., —O-acyl); for example, —O—C(=O)-alkyl.

"Acylamino" is an amino radical having an acyl substituent (i.e., —N-acyl); for example, —NH—C(=O)-alkyl.

"Alkoxyacyl" is an acyl radical (—C(=O)—) having an alkoxy subtituent (i.e., —O—R), for example, —C(=O)—O-alkyl "Alkenyl" is an unsubstituted or substituted hydrocarbon chain radical having from 2 to 15 carbon atoms; preferably from 2 to 10 carbon atoms; more preferably from 4–10; except where indicated. Preferred are alkenyl substituents having at least one olefinic double bond (including, for example, vinyl, allyl and butenyl).

"Alkynyl" is an unsubstituted or substituted hydrocarbon chain radical having from 2 to 15 carbon atoms; preferably from 2 to 10 carbon atoms; more preferably from 4–10; except where indicated. The chain has at least one carbon— carbon triple bond.

"Alkoxy" is an oxygen radical having a hydrocarbon chain substituent, where the hydrocarbon chain is an alkyl or alkenyl (i.e., —O-alkyl or —O-alkenyl). Preferred alkoxy groups include (for example) methoxy, ethoxy, propoxy and allyloxy.

"Alkyl" is an unsubstituted or substituted saturated hydrocarbon chain radical having from 1 to 15 carbon atoms; preferably from 1 to 10 carbon atoms; more preferably 4–10; except where indicated. Preferred alkyl groups include (for example) substituted or unsubstituted methyl, ethyl, propyl, isopropyl, and butyl.

"Alkylamino" is an amino radical having one or two alkyl substituents (i.e., —N-alkyl).

"Aminoacyl" is acyl radical having an amino substituent (i.e., —C(=O)—N); for example, —C(=O)—NH$_2$. The amino group of the aminoacyl moiety may be unsubstituted (i.e., primary amine) or may be substituted with one (secondary amine) or two (i.e., tertiary amine) alkyl groups.

"Aryl" is an aromatic carbocyclic ring radical. Preferred aryl groups include (for example) phenyl, tolyl, xylyl, cumenyl and naphthyl.

"Arylalkyl" is an alkyl radical substituted with an aryl group. Preferred arylalkyl groups include benzyl, phenylethyl, and phenylpropyl.

"Arylamino" is an amine radical substituted with an aryl group (i.e., —NH-aryl).

"Aryloxy" is an oxygen radical having an aryl substituent (i.e., —O-aryl).

"Capable of bearing a charge" refers to a moiety that bears a charge (e.g., quaternary ammonium group) or one that can bear a charge at an appropriate pH (e.g., carboxyl or amino).

"Carbocyclic ring" is an unsubstituted or substituted, saturated, unsaturated or aromatic, hydrocarbon ring radical. Carbocyclic rings are monocyclic or are fused, bridged or spiro polycyclic ring systems. Monocyclic carbocyclic rings generally contain from 3 to 9 atoms, preferably 3 to 6 atoms. However, where $R^4$ and $R^5$ together form a ring, such monocyclic rings preferably contain from 3–13 atoms. Polycyclic carbocyclic rings contain from 7 to 17 atoms, preferably from 7 to 13 atoms.

"Carbocycle-alkyl" is an unsubstituted or substituted alkyl radical substituted with a carbocyclic ring. The carbocyclic ring is preferably an aryl or cycloalkyl; more preferably an aryl. Preferred carbocycle-alkyl groups include benzyl, phenylethyl and phenylpropyl.

"Carbocycle-heteroalkyl" is an unsubstituted or substituted heteroalkyl radical substituted with a carbocyclic ring. The carbocyclic ring is preferably an aryl or cycloalkyl; more preferably an aryl. The heteroalkyl is preferably 2-oxa-propyl, 2-oxa-ethyl, 2-thia-propyl, or 2-thia-ethyl.

"Carbocycle-thio" is a sulfur atom substituted with a carbocyclic ring. The carbocyclic ring is preferably an aryl or cycloalkyl; more preferably an aryl.

"Carboxyalkyl" is an unsubstituted or substituted alkyl radical substituted with with a carboxy (—C(=O)OH) moiety.

"Cycloalkyl" is a saturated carbocyclic ring radical. Preferred cycloalkyl groups include (for example) cyclopropyl, cyclobutyl and cyclohexyl.

"Cycloheteroalkyl" is a saturated heterocyclic ring. Preferred cycloheteroalkyl groups include (for example) morpholine, piperadine, piperazine, and furanyl.

"Fused rings" are rings that are superimposed together such that they share two ring atoms. A given ring may be fused to more than one other ring.

"Heterocycle-alkyl" is an unsubstituted or substituted alkyl radical substituted with a heterocyclic ring. The heterocyclic ring is preferably an aryl or cycloheteroalkyl; more preferably an aryl.

"Heterocycle-heteroalkyl" is an unsubstituted or substituted heteroalkyl radical substituted with a heterocyclic ring. The heterocyclic ring is preferably an aryl or cycloheteroalkyl; more preferably an aryl.

"Heterocycle-thio" is a sulfur atom substituted with a heterocyclic ring. The heterocyclic ring is preferably an aryl or cycloheteroalkyl; more preferably an aryl.

"Heteroatom" is a nitrogen, sulfur or oxygen atom. Groups containing one or more heteroatoms may contain different heteroatoms.

"Heteroalkyl" is an unsubstituted or substituted saturated chain radical having from 3 to 8 members comprising carbon atoms and one or two heteroatoms.

"Heterocyclic ring" is an unsubstituted or substituted, saturated, unsaturated or aromatic ring radical comprised of carbon atoms and one or more heteroatoms in the ring. Heterocyclic rings are monocyclic or are fused, bridged or spiro polycyclic ring systems. Monocyclic heterocyclic rings contain from 3 to 9 atoms, preferably 4 to 7 atoms. Polycyclic rings contain from 7 to 17 atoms, preferably from 7 to 13 atoms.

"Heteroaryl" is an aromatic heterocyclic ring radical. Preferred heteroaryl groups include (for example) thienyl, furyl, pyrrolyl, pyridinyl, pyrazinyl, thiazolyl, pyrimidinyl, quinolinyl, and tetrazolyl.

"Halo", "halogen", or "halide" is a chloro, bromo, fluoro or iodo atom radical. Chloro and fluoro are preferred halides.

Also, as referred to herein, a "lower" hydrocarbon moiety (e.g., "lower" alkyl) is a hydrocarbon chain comprised of from 1 to 6, preferably from 1 to 4, carbon atoms.

A "pharmaceutically-acceptable salt" is a cationic salt formed at any acidic (e.g., carboxyl) group, or an anionic salt formed at any basic (e.g., amino) group. Many such salts are known in the art, as described in World Patent Publication 87/05297, Johnston et al., published Sep. 11, 1987 (incorporated by reference herein). Preferred cationic salts include the alkali metal salts (such as sodium and potassium), and alkaline earth metal salts (such as magnesium and calcium). Preferred anionic salts include the halides (such as chloride salts).

A "biohydrolyzable ester" is an ester of a hydroxamic acid that does not essentially interfere with the inhibitory activity of the compound, or that is readily converted in vivo by a human or lower animal subject to yield an active hydroxamic acid. Such esters include those that do not interfere with the biological activity of the hydroxamic acid. Many such esters are known in the art, as described in World Patent Publication 87/05297, Johnston et al., published Sep. 11, 1987, (incorporated by reference herein). Such esters include lower alkyl esters, lower acyloxy-alkyl esters (such as acetoxymethyl, acetoxyethyl, aminocarbonyloxymethyl, pivaloyloxymethyl and pivaloyloxyethyl esters), lactonyl esters (such as phthalidyl and thiophthalidyl esters), lower alkoxy-acyloxyalkyl esters (such as methoxycarbonyloxymethyl, ethoxycarbonyloxyethyl and isopropoxycarbonyloxyethyl esters), alkoxyalkyl esters, choline esters, and alkyl acylamino alkyl esters (such as acetamidomethyl esters).

A "biohydrolyzable amide" is an amide of a Formula (I) compound that does not interfere with the metalloprotease inhibitory activity of these compounds, or that is readily converted in vivo by a human or lower animal subject to yield an active Formula (I) compound. Such amides include those that do not interfere with the biological activity of the Formula (I) compounds. Many such amides are known in the art, and include: lower alkyl amides (e.g., acetamide, propionamide, etc.), amino acid amides (e.g., glycine amides, alanine amides, proline amides, etc.), polypeptide amides (e.g., alanylalanine amides, glycylproline amides, etc.), alkoxycarbonyl amides (e.g., methoxoycarbonyl amides, benzyloxycarbonyl amides, etc.), and alkylaminocarbonyl amides (e.g., methylaminocarbonyl amides, ethylaminocarbonyl amides, etc.).

A "solvate" is a complex formed by the combination of a solute (e.g., a hydroxamic acid) and a solvent (e.g., water). See J. Honig et al., *The Van Nostrand Chemist's Dictionary*, p. 650 (1953). Pharmaceutically-acceptable solvents used according to this invention include those that do not interfere with the biological activity of the hydroxamic acid (e.g., water, ethanol, acetic acid, N,N- dimethylformamide).

As defined above and as used herein, substituent groups may themselves be substituted. Such substitution may be with one or more substituents. Such substituents include those listed in C. Hansch and A. Leo, *Substituent Constants for Correlation Analysis in Chemistry and Biology* (1979), incorporated by reference herein. Preferred substituents include (for example) alkyl, alkenyl, alkoxy, hydroxy, oxo, nitro, amino, aminoalkyl (e.g., aminomethyl, etc.), cyano, halo, carboxy, alkoxyaceyl (e.g., carboethoxy, etc.), thiol, aryl, cycloalkyl, heteroaryl, heterocycloalkyl (e.g., piperidinyl, morpholinyl, pyrrolidinyl, etc.), imino, thioxo, hydroxyalkyl, aryloxy, arylalkyl, and combinations thereof.

As used herein, "mammalian matrix metalloprotease" means any enzyme found in mammalian sources which is capable of catalyzing the breakdown of collagen, gelatin or proteoglycan under suitable assay conditions. Appropriate assay conditions can be found, for example, in U.S. Pat. No. 4,743,587, which references the procedure of Cawston, et al., Anal Biochem (1979) 99: 340–345, use of a synthetic substrate is described by Weingarten, H., et al., Biochem Biophy Res Comm (1984) 139: 1184–1187. Any standard method for analyzing the breakdown of these structural proteins can, of course, be used. The matrix metalloprotease enzymes referred to herein are all zinc-containing proteases which are similar in structure to, for example, human stromelysin or skin fibroblast collagenase. The ability of candidate compounds to inhibit matrix metalloprotease activity can, of course, be tested in the assays described above. Isolated matrix metalloprotease enzymes can be used to confirm the inhibiting activity of the invention compounds, or crude extracts which contain the range of enzymes capable of tissue breakdown can be used.

Compounds:

The following is a representative, not exhausitive, list of preferred compounds within the scope of the invention.

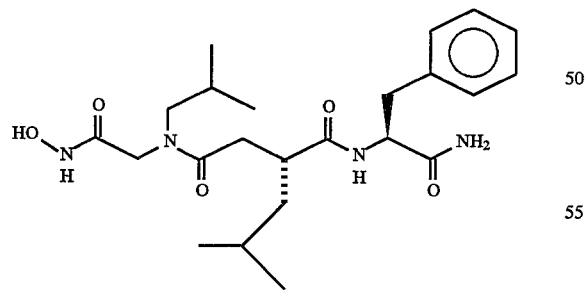

-continued

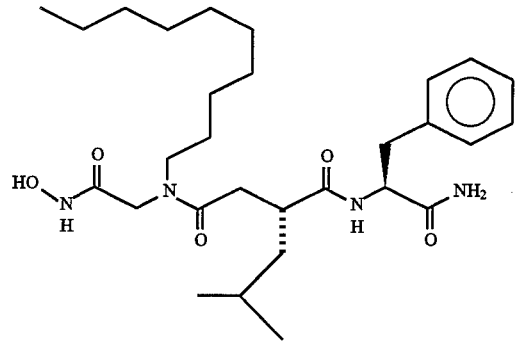

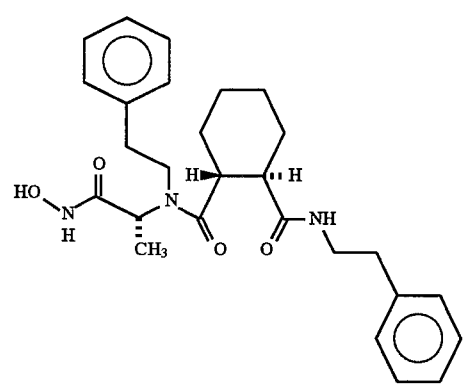

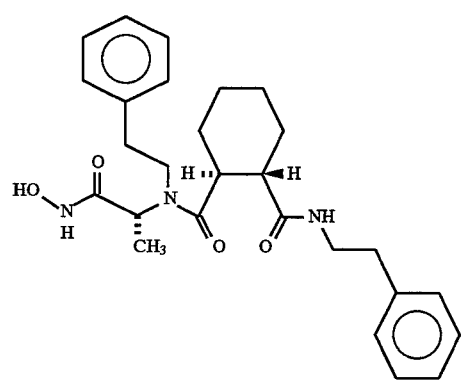

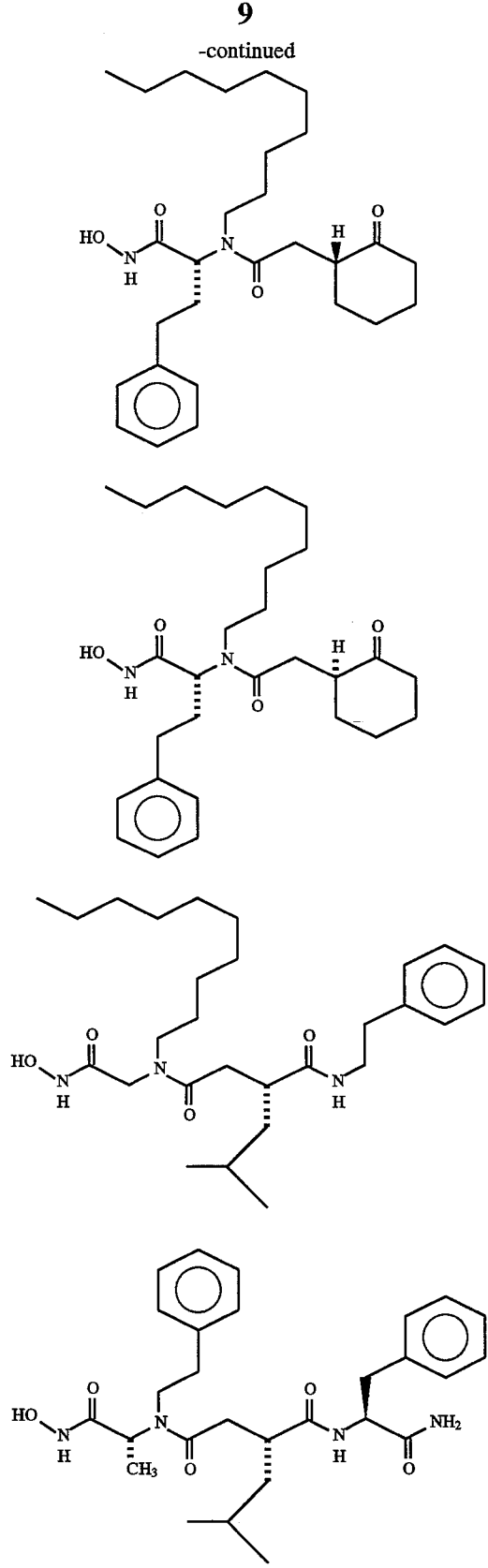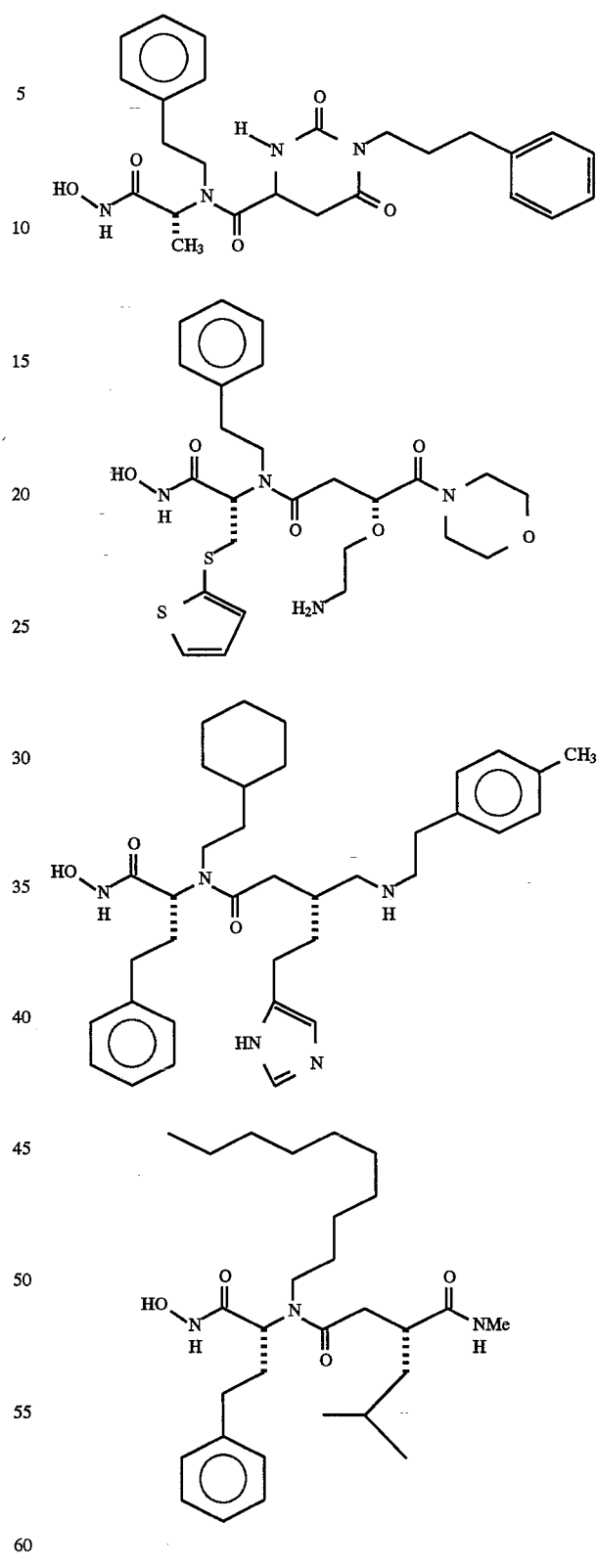

11
-continued
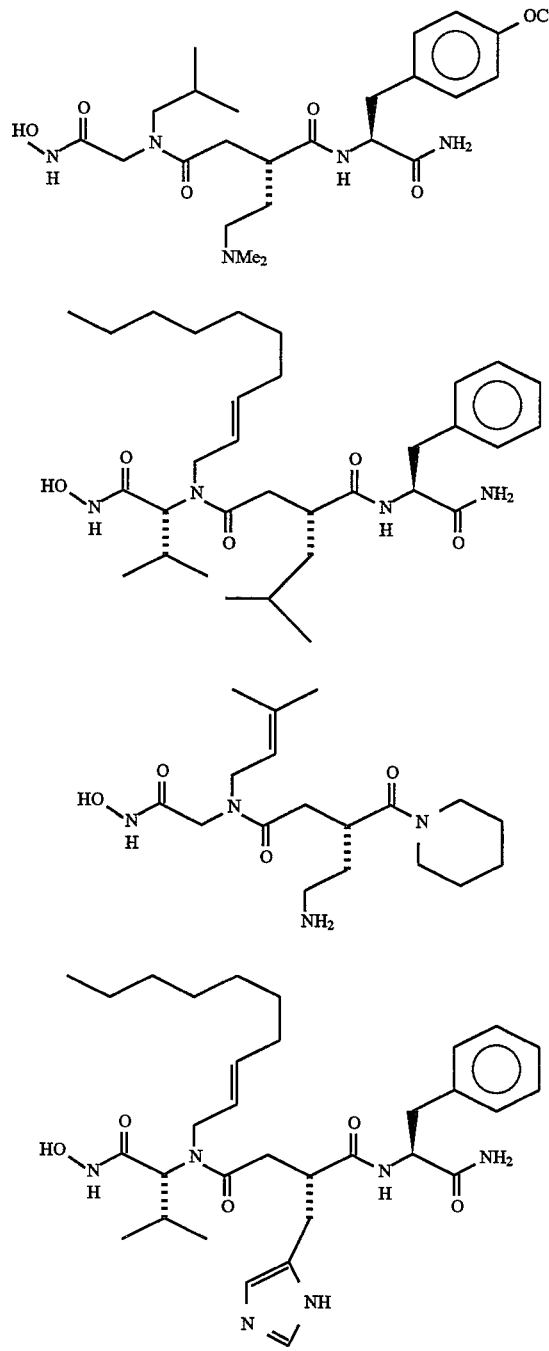
12
-continued
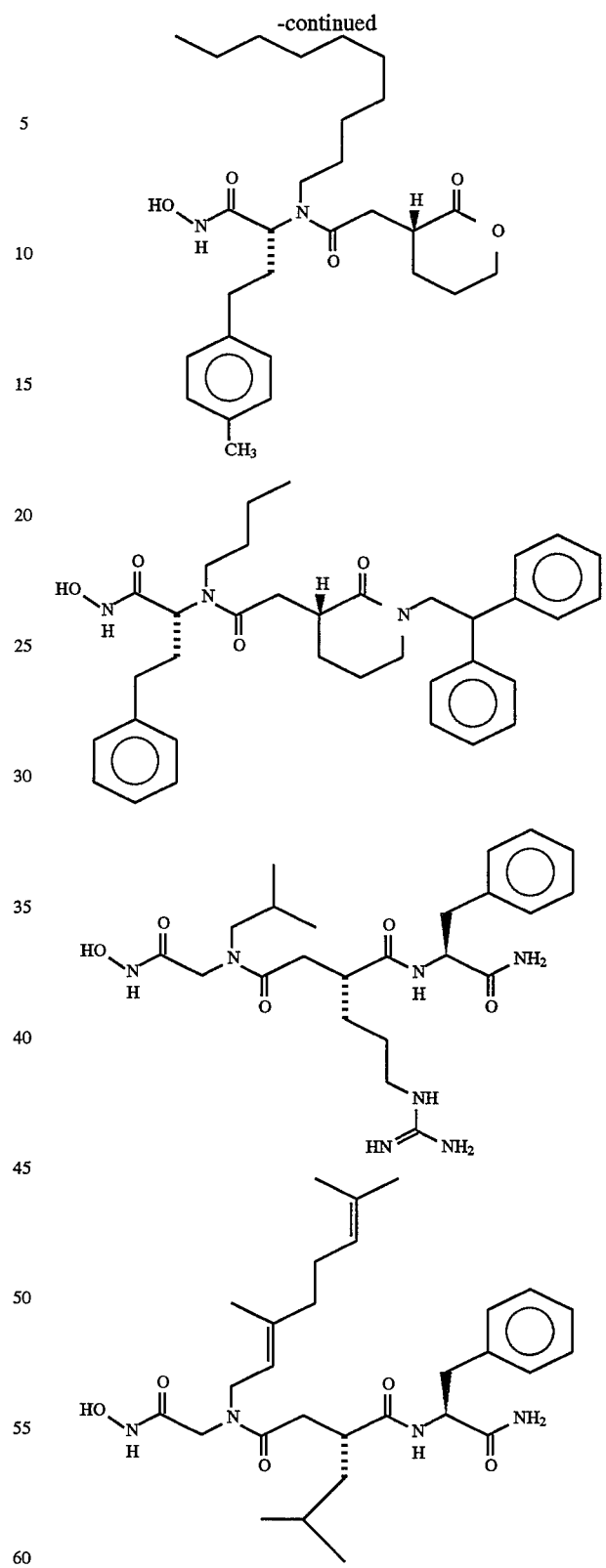

13
-continued
14
-continued
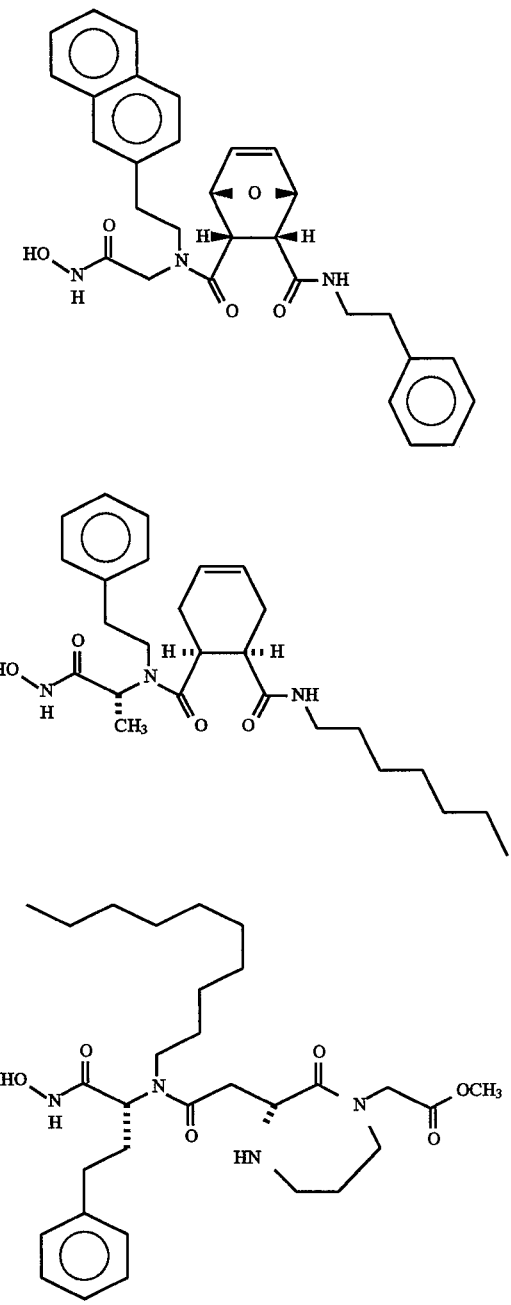
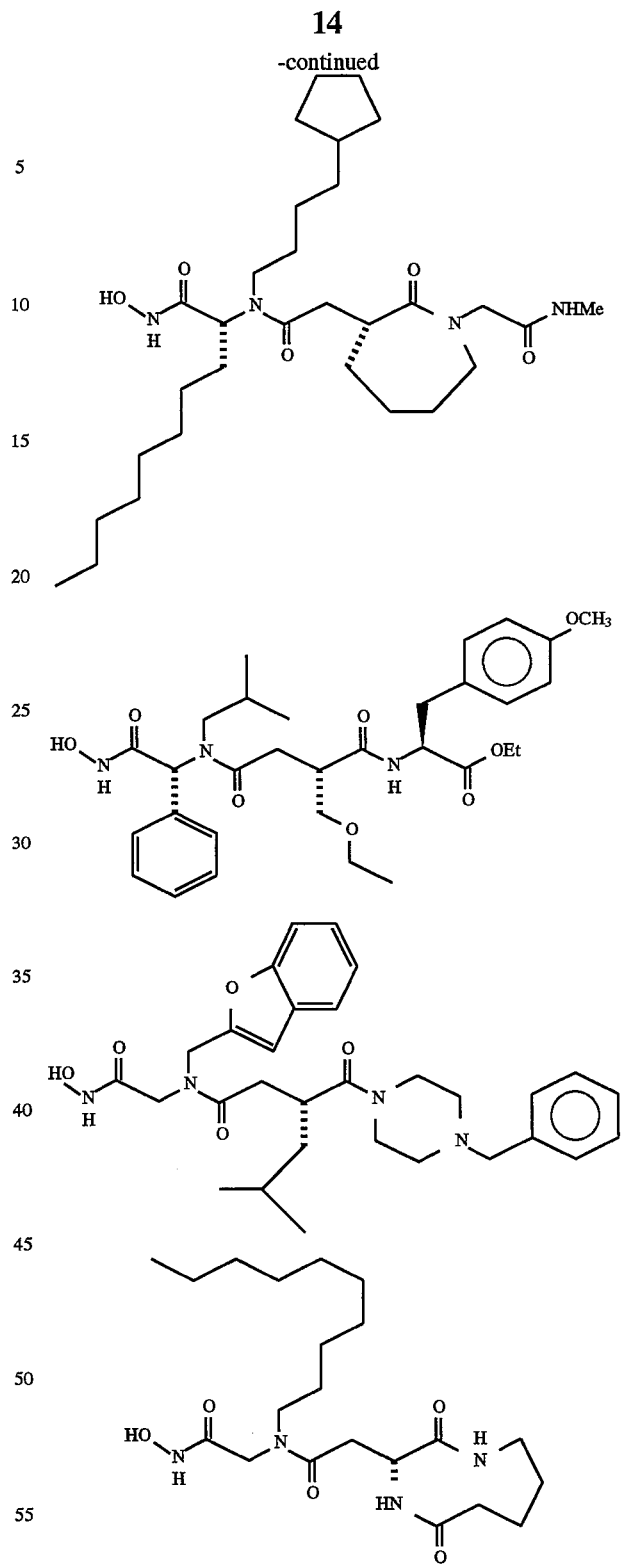

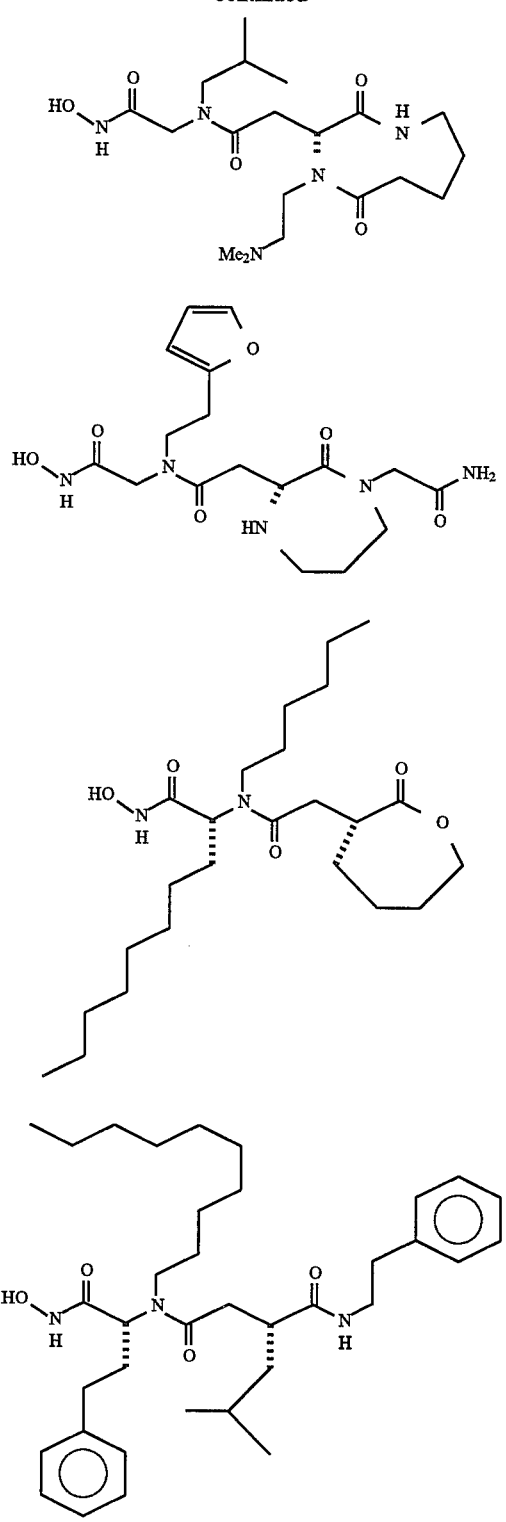
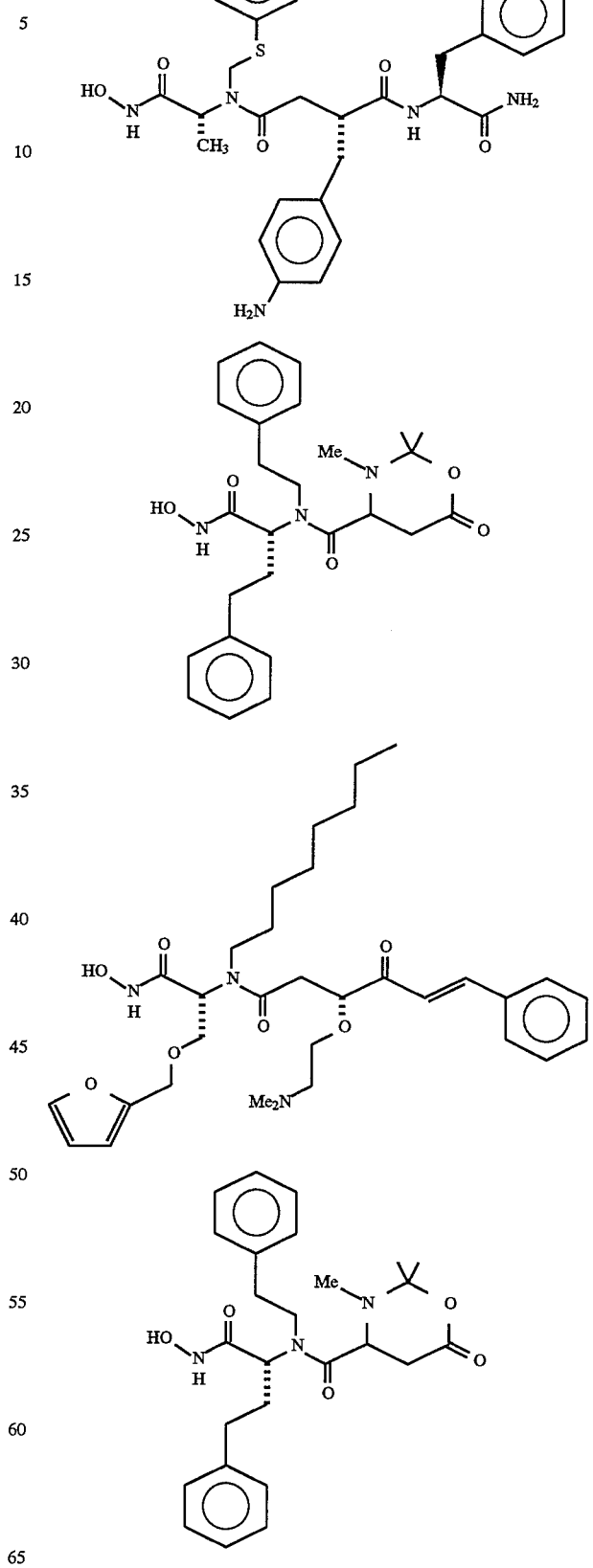

17
-continued
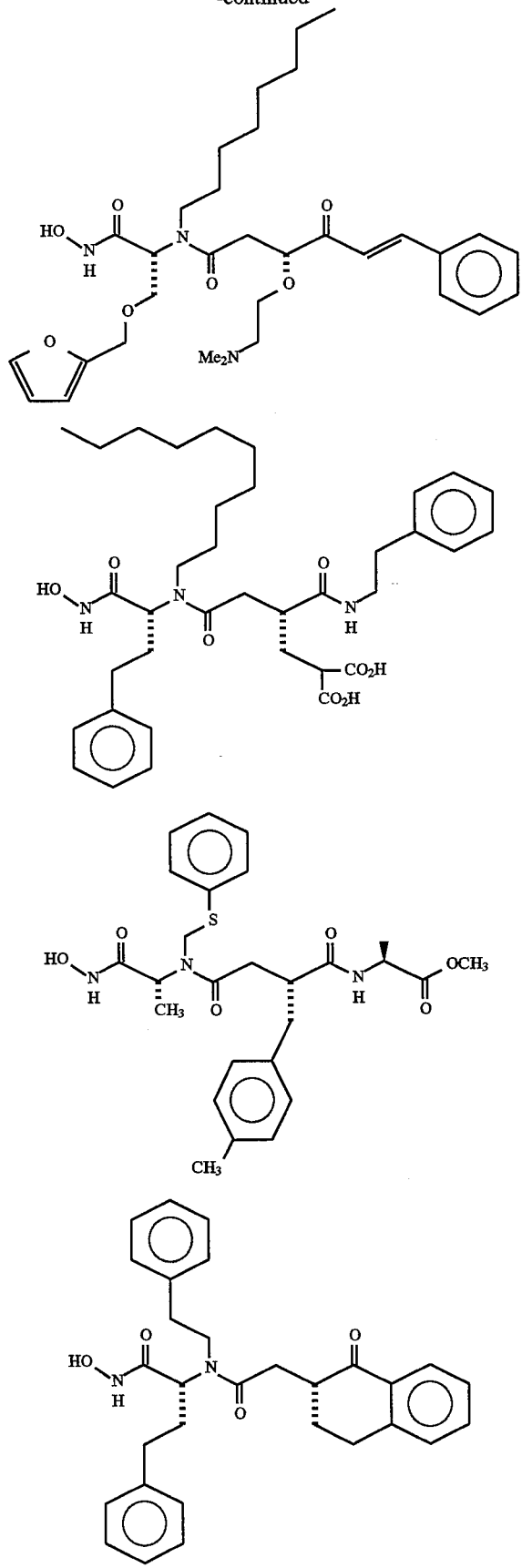
18
-continued
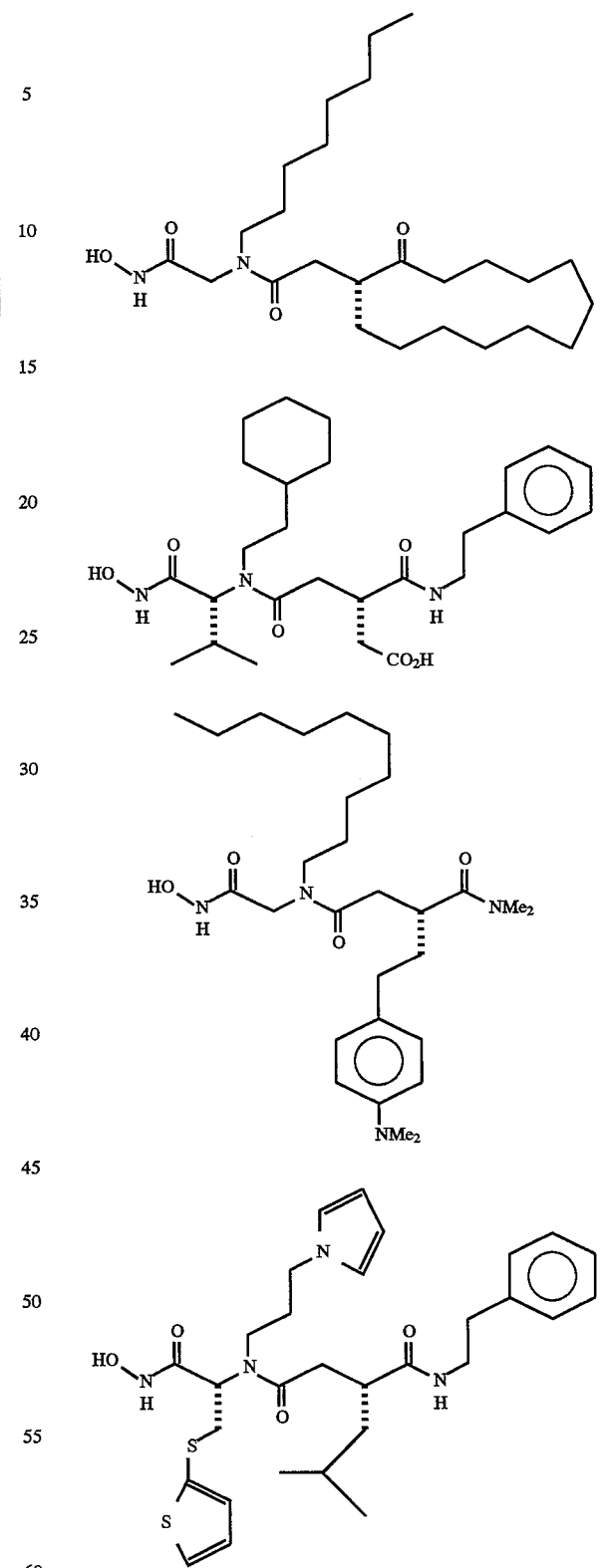

19
-continued
20
-continued
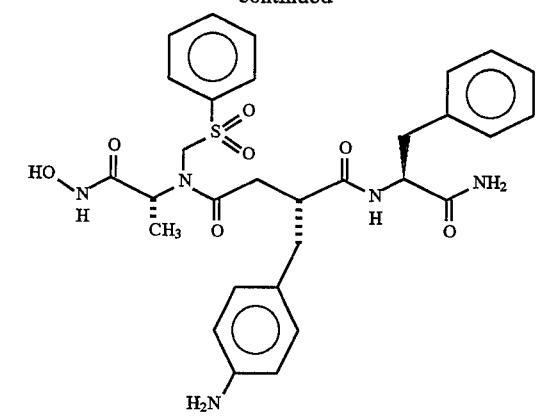
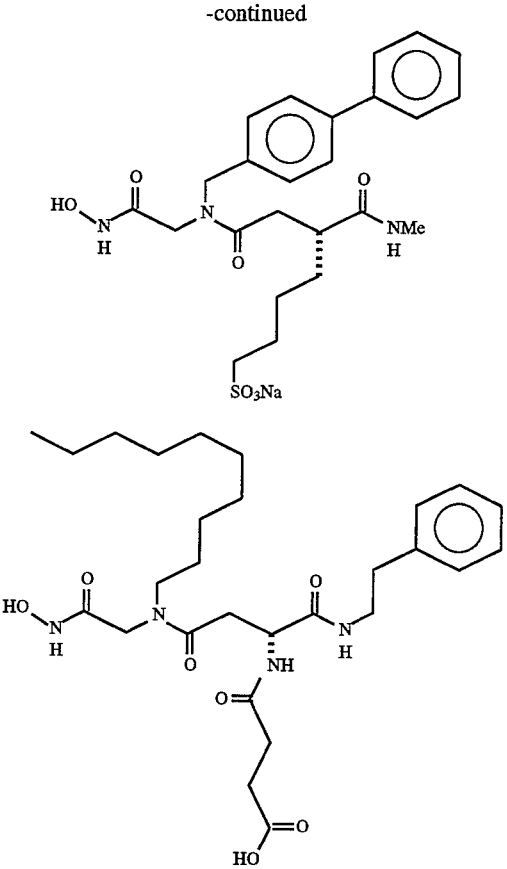
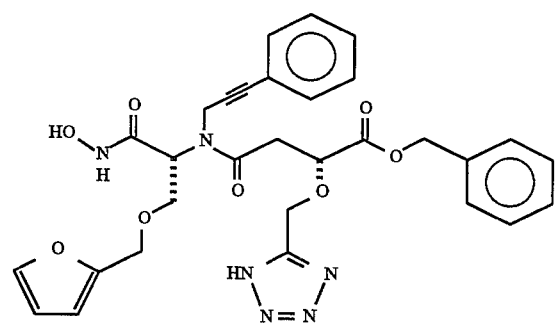
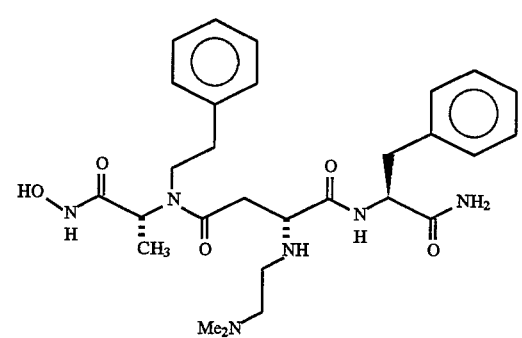
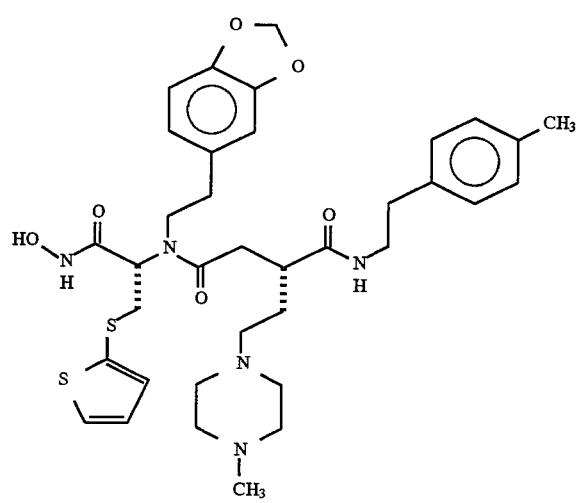
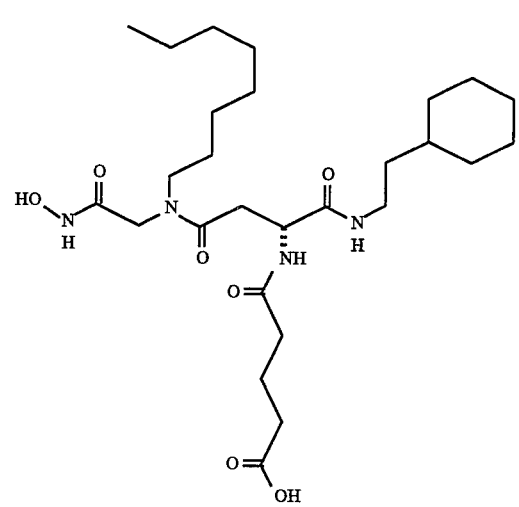

21
-continued
22
-continued
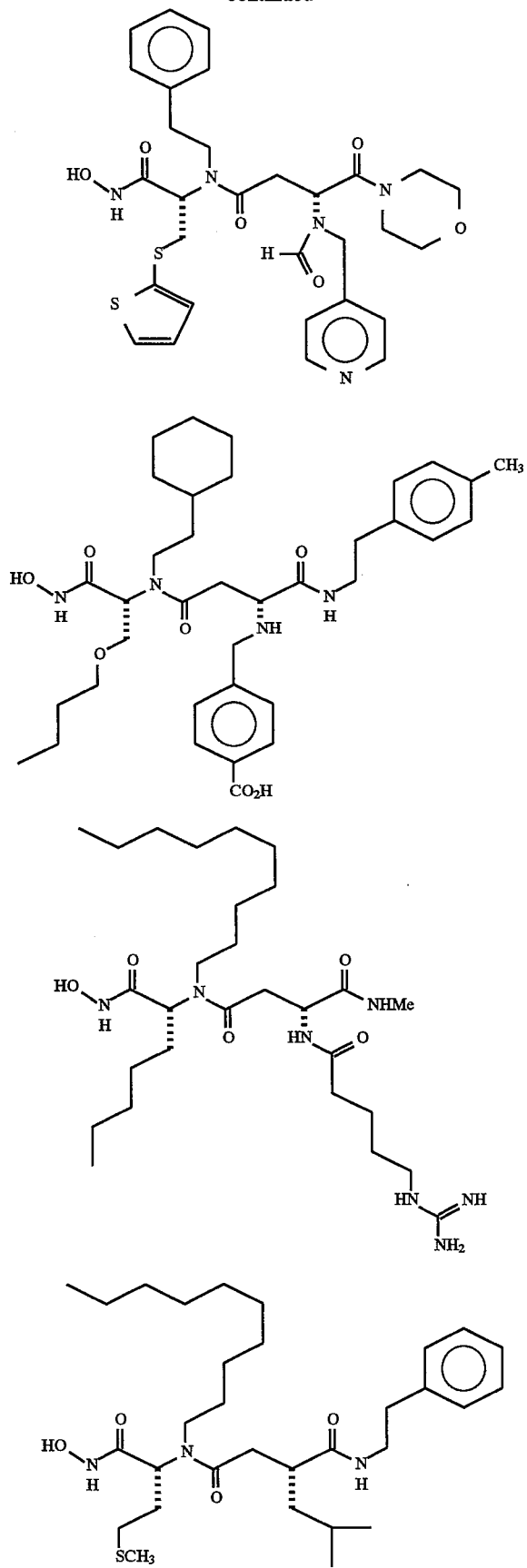
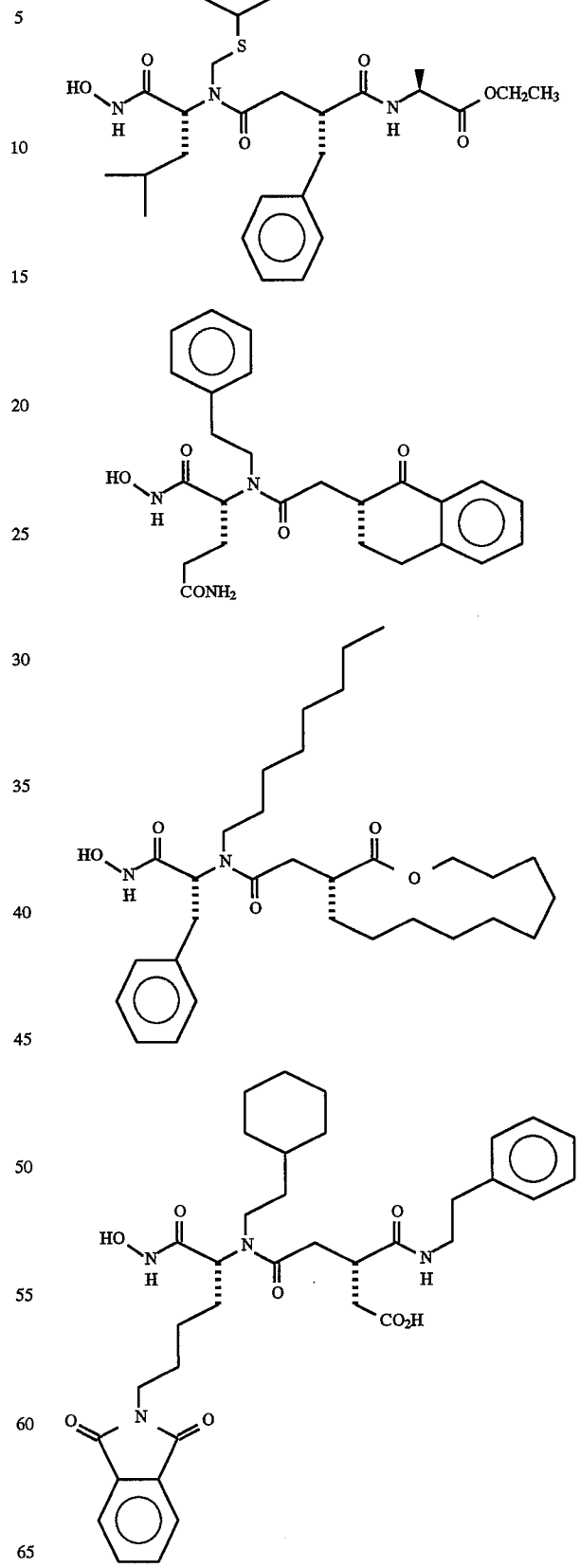

-continued

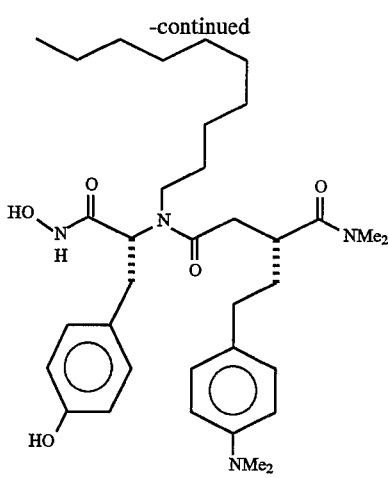

In general, the hydroxamic compounds of Formula (I) can be prepared by the following procedure. A suitably protected hydroxamic acid (O-protected or N, O-protected) derived from an N-alkyl glycine or N-alkyl D-amino acid is coupled with an appropriately substituted carboxylic acid. Various carbodiimide reagents may be employed, as well as mixed anhydride methods, or other coupling methods commonly used in peptide couplings. The desired compounds are obtained after removal of protecting groups by the appropriate chemistry.

Compositions:

The compositions of the invention comprise:

(a) a safe and effective amount of a compound of Formula (I); and (b) a pharmaceutically-acceptable carrier.

As discussed above, numerous diseases are known to be mediated by excess or undesired matrix-destroying metalloprotease activity. These include tumor metastasis, osteoarthritis, rheumatoid arthritis, skin inflammation, ulcerations, particularly of the cornea, reaction to infection, periodontitis and the like. Thus, the compounds of the invention are useful in therapy with regard to conditions involving this unwanted activity.

The invention compounds can therefore be formulated into pharmaceutical compositions for use in treatment or prophylaxis of these conditions. Standard pharmaceutical formulation techniques are used, such as those disclosed in Remington's Pharmaceutical Sciences, Mack Publishing Company, Easton, Pa., latest edition.

A "safe and effective amount" of a Formula (I) compound is an amount that is effective, to inhibit matrix metalloproteases at the site(s) of activity, in a human or lower animal subject, without undue adverse side effects (such as toxicity, irritation, or allergic response), commensurate with a reasonable benefit/risk ratio when used in the manner of this invention. The specific "safe and effective amount" will, obviously, vary with such factors as the particular condition being treated, the physical condition of the patient, the duration of treatment, the nature of concurrent therapy (if any), the specific dosage form to be used, the carrier employed, the solubility of the Formula (I) compound therein, and the dosage regimen desired for the composition.

The compositions of this invention are preferably provided in unit dosage form. As used herein, a "unit dosage form" is a composition of this invention containing an amount of a Formula (I) compound that is suitable for administration to a human or lower animal subject, in a single dose, according to good medical practice. These compositions preferably contain from about 5 mg (milligrams) to about 1000 mg, more preferably from about 10 mg to about 500 mg, more preferably from about 10 mg to about 300 mg, of a Formula (I) compound.

The compositions of this invention may be in any of a variety of forms, suitable (for example) for oral, rectal, topical or parenteral administration. Depending upon the particular route of administration desired, a variety of pharmaceutically-acceptable carriers well-known in the art may be used. These include solid or liquid fillers, diluents, hydrotropes, surface-active agents, and encapsulating substances. Optional pharmaceutically-active materials may be included, which do not substantially interfere with the inhibitory activity of the Formula (I) compound. The amount of carrier employed in conjunction with the Formula (I) compound is sufficient to provide a practical quantity of material for administration per unit dose of the Formula (I) compound. Techniques and compositions for making dosage forms useful in the methods of this invention are described in the following references, all incorporated by reference herein: Modern Pharmaceutics, Chapters 9 and 10 (Banker & Rhodes, editors, 1979); Lieberman et al., Pharmaceutical Dosage Forms: Tablets (1981); and Ansel, Introduction to Pharmaceutical Dosage Forms 2d Edition (1976).

In particular, pharmaceutically-acceptable carriers for systemic administration include sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Preferred carriers for parenteral administration include propylene glycol, ethyl oleate, pyrrolidone, ethanol, and sesame oil. Preferably, the pharmaceutically-acceptable carrier, in compositions for parenteral administration, comprises at least about 90% by weight by the total composition.

Various oral dosage forms can be used, including such solid forms as tablets, capsules, granules and bulk powders. These oral forms comprise a safe and effective amount, usually at least about 5%, and preferably from about 25% to about 50%, of the Formula (I) compound. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents. Preferred carriers for oral administration include gelatin, propylene glycol, cottonseed oil and sesame oil.

The compositions of this invention can also be administered topically to a subject, i.e., by the direct laying on or spreading of the composition on the epidermal or epithelial tissue of the subject. Such compositions include, for example, lotions, creams, solutions, gels and solids. These topical compositions preferably comprise a safe and effective amount, usually at least about 0.1%, and preferably from about 1% to about 5%, of the Formula (I) compound. Suitable carries for topical administration preferably remain in place on the skin as a continuous film, and resist being removed by perspiration or immersion in water. Generally, the carrier is organic in nature and capable of having dispersed or dissolved therein the Formula (I) compound. The carrier may include pharmaceutically-acceptable emolients, emulsifiers, thickening agents, and solvents.

Methods of Administration:

This invention also provides methods of treating or preventing disorders associated with excess or undesired matrix metalloprotease activity in a human or other animal subject, by administering a safe and effective amount of a Formula (I) compound to said subject. As used herein, a "disorder associated with excess or undesired matrix metalloprotease activity" is any disorder characterized by degradation of matrix proteins. The methods of the invention are useful in treating disorders such as (for example) osteoarthritis, periodontitis, corneal ulceration, tumor invasion, rheumatoid arthritis, etc.

The Formula (I) compounds and compositions of this invention can be administered topically or systemically. Systemic application includes any method of introducing Formula (I) compound into the tissues of the body, e.g., intra-articular (especially in treatment of rheumatoid arthritis), intrathecal, epidural, intramuscular, transdermal, intravenous, intraperitoneal, subcutaneous, sublingual, rectal, and oral administration. The Formula (I) compounds of the present invention are preferably administered orally.

The specific dosage of inhibitor to be administered, as well as the duration of treatment, are mutually dependent. The dosage and treatment regimen will also depend upon such factors as the specific Formula (I) compound used, the treatment indication, the ability of the Formula (I) compound to reach minimum inhibitory concentrations at the site of the matrix metalloprotease to be inhibited, the personal attributes of the subject (such as weight), compliance with the treatment regimen, and the presence and severity of any side effects of the treatment.

Typically, for a human adult (weighing approximately 70 kilograms), from about 5 mg to about 3000 mg, more preferably from about 5 mg to about 1000 mg, more preferably from about 10 mg to about 100 mg, of Formula (I) compound are administered per day. It is understood that these dosage ranges are by way of example only, and that daily administration can be adjusted depending on the factors listed above.

A preferred method of administration for treatment of rheumatoid arthritis is oral or parenterally via intra-articular injection. As is known and practiced in the art, all formulations for parenteral administration must be sterile. For mammals, especially humans, (assuming an approximate body weight of 70 kilograms) individual doses of from about 10 mg to about 1000 mg are preferred.

A preferred method of systemic administration is oral. Individual doses of from about 10 mg to about 1000 mg, preferably from about 10 mg to about 300 mg are preferred.

Topical administration can be used to deliver the Formula (I) compound systemically, or to treat a subject locally. The amounts of Formula (I) compound to be topically administered depends upon such factors as skin sensitivity, type and location of the tissue to be treated, the composition and carrier (if any) to be administered, the particular Formula (I) compound to be administered, as well as the particular disorder to be treated and the extent to which systemic (as distinguished from local) effects are desired.

For indications to be treated systemically, it is preferred that the compounds be orally administered. These conditions include rheumatoid arthritis, osteoarthritis and tumor metastasis.

The inhibitors of the invention can be targeted to specific locations where the matrix metalloprotease is accumulated by using targeting ligands. For example, to focus the inhibitors to matrix metalloprotease contained in a tumor, the inhibitor is conjugated to an antibody or fragment thereof which is immunoreactive with a tumor marker as is generally understood in the preparation of immunotoxins in general. The targeting ligand can also be a ligand suitable for a receptor which is present on the tumor. Any targeting ligand which specifically reacts with a marker for the intended target tissue can be used. Methods for coupling the invention compound to the targeting ligand are well known and are similar to those described below for coupling to carrier. The conjugates are formulated and administered as described above.

For localized conditions, topical administration is preferred. For example, to treat ulcerated cornea, direct application to the affected eye may employ a formulation as eyedrops or aerosol. For corneal treatment, the compounds of the invention can also be formulated as gels or ointments, or can be incorporated into collagen or a hydrophilic polymer shield. The materials can also be inserted as a contact lens or reservoir or as a subconjunctival formulation. For treatment of skin inflammation, the compound is applied locally and topically, in a gel, paste, salve or ointment. The mode of treatment thus reflects the nature of the condition and suitable formulations for any selected route are available in the art.

In all of the foregoing, of course, the compounds of the invention can be administered alone or as mixtures, and the compositions may further include additional drugs or excipients as appropriate for the indication.

Some of the compounds of the invention also inhibit bacterial metalloproteases although generally at a lower level than that exhibited with respect to mammalian metalloproteases. Some bacterial metalloproteases seem to be less dependent on the stereochemistry of the inhibitor, whereas substantial differences are found between diastereomers in their ability to inactivate the mammalian proteases. Thus, this pattern of activity can be used to distinguish between the mammalian and bacterial enzymes.

Preparation and Use of Antibodies:

The invention compounds can also be utilized in immunization protocols to obtain antisera immunospecific for the invention compounds. As the invention compounds are relatively small, they are advantageously coupled to antigenically neutral carries such as the conventionally used keyhole limpet hemocyanin (KLH) or serum albumin carries. For those invention compounds having a carboxyl functionality, coupling to carrier can be done by methods generally known in the art. For example, the carboxyl residue can be reduced to an aldehyde and coupled to carrier through reaction with sidechain amino groups in protein-based carries, optionally followed by reduction of imino linkage formed. The carboxyl residue can also be reacted with sidechain amino groups using condensing agents such as dicyclohexyl carbodiimide or other carbodiimide dehydrating agents.

Linker compounds can also be used to effect the coupling; both homobifunctional and heterobifunctional linkers are available from Pierce Chemical Company, Rockford, Ill. The resulting immunogenic complex can then be injected into suitable mammalian subjects such as mice, rabbits, and the like. Suitable protocols involve repeated injection of the immunogen in the presence of adjuvants according to a schedule which boosts production of antibodies in the serum. The titers of the immune serum can readily be measured using immunoassay procedures, now standard in the art, employing the invention compounds as antigens.

The antisera obtained can be used directly or monoclonal antibodies may be obtained by harvesting the peripheral blood lymphocytes or the spleen of the immunized animal and immortalizing the antibody-producing cells, followed by identifying the suitable antibody producers using standard immunoassay techniques.

The polyclonal or monoclonal preparations are then useful in monitoring therapy or prophylaxis regimens involving the compounds of the invention. Suitable samples such as those derived from blood, serum, urine, or saliva can be tested for the presence of the administered inhibitor at various times during the treatment protocol using standard immunoassay techniques which employ the antibody preparations of the invention.

The invention compounds can also be coupled to labels such as scintigraphic labels, e.g., technetium 99 or I-131, using standard coupling methods. The labeled compounds are administered to subjects to determine the locations of excess amounts of one or more matrix metalloproteases in vivo. The ability of the inhibitors to selectively bind matrix metalloprotease is thus taken advantage of to map the distribution of these enzymes in situ. The techniques can also be employed in histological procedures and the labeled invention compounds can be used in competitive immunoassays.

The following non-limiting examples illustrate the compounds, compositions, processes, and uses of the present invention.

EXAMPLE 1

Synthesis of 3-{N-[(N-Hydroxyaminocarbonyl)methyl]-N-isobutylaminocarbonyl }-2-(R)-isobutylpropanoyl-L-phenylalanine amide

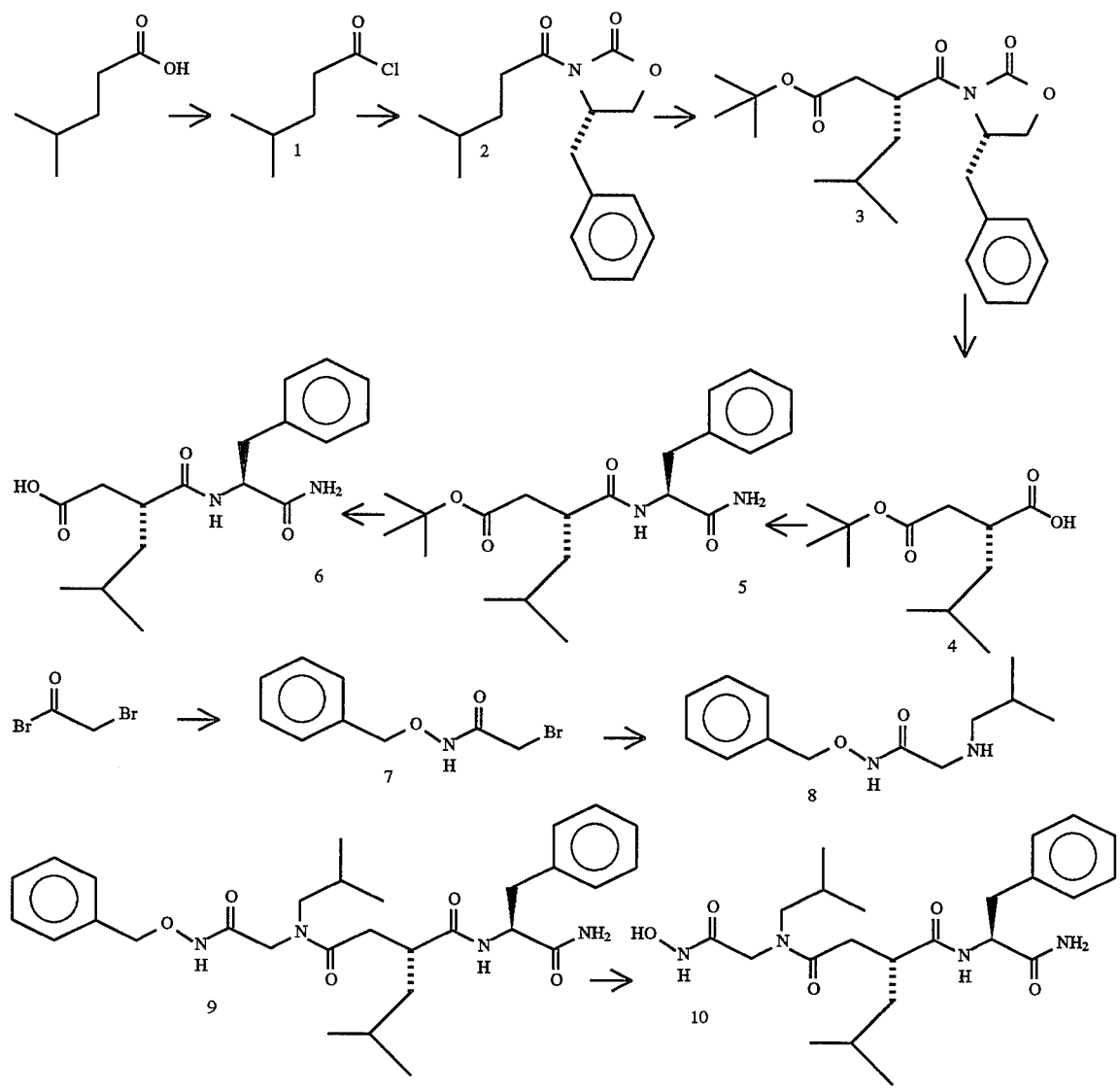

4-Methyl valeric acid (150 g, 1.3 mol) is dissolved in 150 mL of benzene. Oxalyl chloride (163 g, 1.3 mol) is added slowly, the mixture is heated to 50° C. and stirred 1.5 h. The product is distilled at 140°–145° C. to give 1.

(S)-4-Benzyl-2-oxazolidinone (100 g, 565 mmol) is dissolved in tetrahydrofuran (THF) (800 mL) under argon and cooled to −78° C. n-Butyllithium (250 mL, 620 mmol, 2.5M in hexanes) is added dropwise, and the mixture is stirred 15 min. After 4-methyl valeroyl chloride, 1, (83.4 g, 85.7 mL, 620 mmol) is slowly added and stirring is continued for 2 h;

the reaction is quenched with ammonium chloride and extracted with ethyl acetate. The product is purified using 4:1 hexane:EtOAc on a silica gel column to give 2.

A solution of 2 (50 g, 181.8 mmol) in THF (100 mL) is cooled to −78° C. under argon. Lithium bis(trimethylsilyl) amide (200 mL, 200 mmol, 1M in THF) is added slowly, and the mixture is stirred for 10 min. t-Butylbromoacetate (29.5 mL, 200 mmol) is slowly added and after 3.5 h the reaction is warmed to −10° C. and stirred an additional 1.5 h. The reaction is quenched with ammonium chloride and extracted with ethyl acetate. The product is purified using 7:1 hexane:EtOAc on a silica gel column to give 3.

A solution of 3 (9.725 g, 25 mmol) in 4:1 THF-water (125 mL) is cooled to 0° C. under argon. Aqueous hydrogen peroxide (30%, 10.2 mL, 100 mmol) is added via syringe, then LiOH.H$_2$O (1.64 g, 40 mmol) in 50 mL H$_2$O is added. After 1.5 hr sodium sulfite (12.6 g, 100 mmol) in water (75 mL) is slowly added. This mixture is extracted 3 times with methylene chloride. The aqueous layer is acidified (pH=2) with HCl and extracted 4 times with ethyl acetate. The ethyl acetate layer is washed with brine and dried over magnesium sulfate. After filtering, the ethyl acetate is removed in vacuo to give 4.

A mixture of 0.230 g (1.00 mmol) of 4, 0.135 g (1.00 mmol) of 1-hydroxybenzotriazole, 0.127 mL (1.00 mmol) of 4-ethylmorpholine, and 0.164 g (1.00 mmol) of phenylalanine amide are stirred in 2 mL of N,N-dimethylformamide (DMF) at room temperature under an inert atmosphere as 0.192 g (1.00 mmol) of 1-(3-dimethylaminopropyl)-3-ethylcarbodiimide hydrochloride is added. The mixture is stirred for 24 h and concentrated under reduced pressure. The residue is taken up in ethyl acetate plus dichloromethane and the organic solution is extracted twice with 1M hydrochloric acid solution, twice with 1M sodium hydroxide solution, once with water, and once with brine. The organic layer is dried over sodium sulfate, filtered, and concentrated under reduced pressure to provide 5.

The t-butyl ester 5 (0.376 g, 1.00 mmol) is dissolved in 3.5 mL of trifluoroacetic acid and allowed to stand for 1 h at room temperature. Removal of the trifluoroacetic acid under reduced pressure provides the product 6.

A mixture of 20.0 g (0.125 mole) of O-benzylhydroxylamine hydrochloride and 35.0 mL (25.4 g, 0.251 mole) of triethylamine in 300 mL of dichloromethane is cooled to −78° C. Bromoacetyl bromide (11.0 mL, 25.5 g, 0.126 mole) is added to the mixture slowly, and the solution is stirred for an additional 45 min at −78° C. after the addition is complete. The solution is extracted twice with water, the organic layer is dried over sodium sulfate, filtered, and concentrated under reduced pressure. The residue is treated with a 1:1 mixture of hexane and ethyl acetate, and the resulting precipitate of 7 is isolated by filtration.

A solution containing 1.5 g of 7 (6.15 mmol) in 20 mL of DMF is cooled in an ice bath as 0.84 mL (0.61 g, 6.0 mmol) of triethylamine is added. After the addition of 0.92 mL (0.68 g, 9.2 mmol) of isobutylamine to the chilled solution the mixture is stirred an additional 45 min before diluting with 100 mL of water. The mixture is extracted with ethyl acetate, then the organic layer is dried over sodium sulfate, filtered, and concentrated under reduced pressure to provide 8.

A mixture of 0.320 g (1.00 mmol) of 6, 0.135 g (1.00 mmol) of 1-hydroxybenzotriazole, 0.127 mL of 4-ethylmorpholine, and 0.236 g (1.00 mmol) of 8 are stirred in 2 mL of DMF at room temperature under an inert atmosphere as 0.192 g (1.00 mmol) of 1-(3-dimethylaminopropyl)-3-ethylcarbodiimide hydrochloride is added. The mixture is stirred for 24 h and concentrated under reduced pressure. The residue is taken up in ethyl acetate plus dichloromethane and the organic solution is extracted twice with 1M hydrochloric acid solution, twice with 1M sodium hydroxide solution, once with water, and once with brine. The organic layer is dried over sodium sulfate, filtered, and concentrated under reduced pressure to provide 9.

A solution of 0.553 g (1.00 mmol) of 9 in 20 mL of methanol is subjected to hydrogenolysis using 0.10 g of 10% palladium on carbon under one atmosphere of hydrogen. The catalyst is removed by filtration and 10 is isolated after concentration under reduced pressure.

EXAMPLE 2

Synthesis of 3-{N-[(N-Hydroxyaminocarbonyl) methyl]-N-decylaminocarbonyl}-2-(R)-isobutylpropanoyl-L-phenylalanine amide (5).

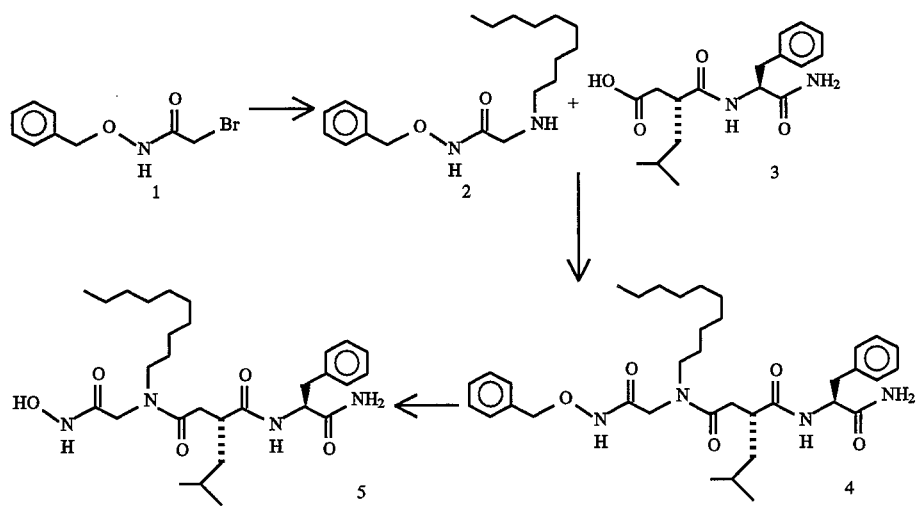

A solution containing 2.36 g of decylamine (15.0 mmol) and 0.84 mL (0.61 g, 6.0 mmol) of triethylamine in 15 mL of N,N-dimethylformamide (DMF) is cooled in an ice bath and stirred. Dropwise addition of 1.22 g (5.0 mmol) of 1 (made according the method used to make Compound 7 in Example 1 ) to the chilled solution is followed an additional 45 min of stirring before removing the ice bath. After an additional 30 min of stirring the mixture is diluted with 100 mL of water. The mixture is extracted with ethyl acetate, then the organic layer is dried over sodium sulfate, filtered, and concentrated under reduced pressure. The residue is purified by column chromatography (silica gel) eluting with dichloromethane/isopropanol mixtures to provide 2.

A mixture of 0.320 g (1.00 mmol) of 3 (made according the method used to make Compound 6 in Example 1), 0,135 g (1.00 mmol) of 1-hydroxybenzotriazole, 0.127 mL of 4-ethylmorpholine, and 0.320 g (1.00 mmol) of 2 are stirred in 2 mL of DMF at room temperature under an inert atmosphere as 0.192 g (1.00 mmol) of 1-(3-dimethylaminopropyl)-3-ethylcarbodiimide hydrochloride is added. The mixture is stirred for 24 h and concentrated under reduced pressure. The residue is taken up in ethyl acetate plus dichloromethane and the organic solution is extracted twice with 1M hydrochloric acid solution, twice with 1M sodium hydroxide solution, once with water, and once with brine. The organic layer is dried over sodium sulfate, filtered, and concentrated under reduced pressure to provide a residue which is purified by column chromatography (silica gel) eluting with dichloromethane/isopropanol mixtures to give 4.

A solution of 0.300 g (0.48 mmol) of 4 in 20 mL of methanol is subjected to hydrogenolysis using 0.10 g of 10% palladium on carbon under one atmosphere of hydrogen. The catalyst is removed by filtration and 5 is isolated after concentration under reduced pressure.

EXAMPLE 3

Synthesis of 3-{N-[(N-Hydroxyaminocarbonyl) methyl]-N-decylaminocarbonyl}-2-(R)-isobutylpropanoic acid, 2-phenylethyl amide (6).

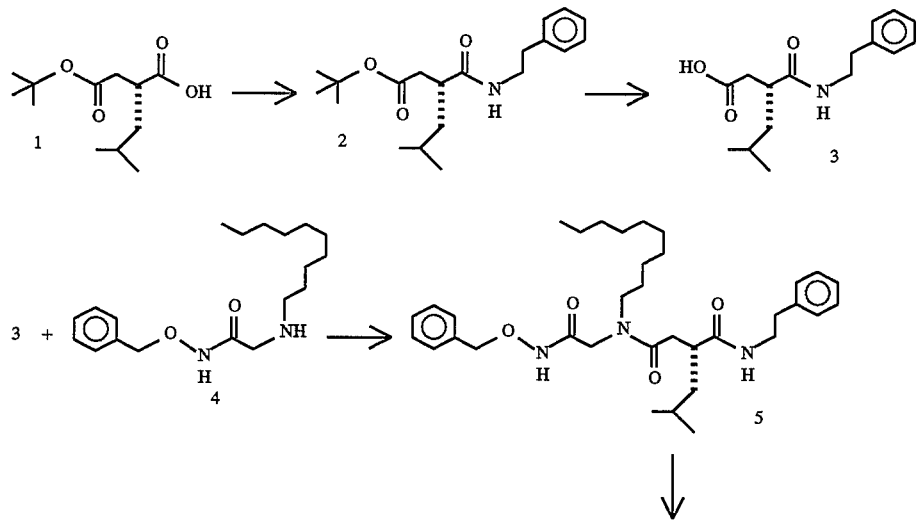

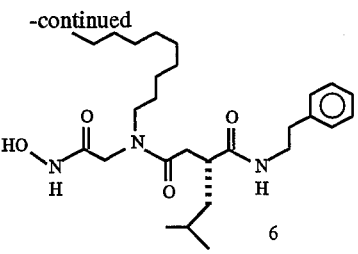

A mixture of 0.230 g (1.00 mmol) of 1 (made according the method used to make Compound 4 in Example 1), 0.135 g (1.00 mmol) of 1-hydroxybenzotriazole, 0.127 mL of 4-ethylmorpholine, and 0.121 g (1.00 mmol) of phenethylamine are stirred in 2 mL of DMF at room temperature under an inert atmosphere as 0.192 g (1.00 mmol) of 1-(3-dimethylaminopropyl)-3-ethylcarbodiimide hydrochloride is added. The mixture is stirred for 24 h and concentrated under reduced pressure. The residue is taken up in ethyl acetate plus dichloromethane and the organic soulution is extracted twice 1M hydrochloric acid solution, twice with 1M sodium hydroxide solution, once with water, and once with brine. The organic layer is dried over sodium sulfate, filtered, and concentrated under reduced pressure to provide 2.

The t-butyl ester 2 (0.315g, 0.94 mmol) is dissolved in 3.5 mL of trifluoroacetic acid and allowed to stand for 1 h at room temperature. Removal of the trifluoroacetic acid under reduced pressure provides the product 3.

A mixture of 0.250 g (0.90 mmol) of 3, 0.135 g (1.00 mmol) of 1-hydroxybenzotriazole, 0.127 mL (1.0 mmol) of 4-ethylmorpholine, and 0.320 g (1.00 mmol) of 4 (made according the method used to make Compound 2 in Example 2) are stirred in 2 mL of DMF at room temperature under an inert atmosphere as 0.192 g (1.00 mmol) of 1-(3-dimethylaminopropyl)-3-ethylcarbodiimide hydrochloride is added. The mixture is stirred for 24 h and concentrated under reduced pressure. The residue is taken up in ethyl acetate plus dichloromethane and the organic solution is extracted twice with 1M hydrochloric acid solution, twice with 1M sodium hydroxide solution, once with water, and once with brine. The organic layer is dried over sodium sulfate, filtered, and concentrated under reduced pressure to provide a residue which is purified by column chromatography (silica gel) eluting with dichloromethane/isopropanol mixtures to give 5.

A solution of 0.111 g (0.22 mmol) of 5 in 5 mL of methanol is subjected to hydrogenolysis using 0.040 g of 10% palladium on carbon under one atmosphere of hydrogen. The catalyst is removed by filtration and 6 is isolated after concentration under reduced pressure.

EXAMPLE 4

Synthesis of 3-{N-[1-(R)-(N-Hydroxyaminocarbonyl)ethyl]-N-(2-phenylethyl)aminocarbonyl}-2-(R)-isobutylpropanoyl-L-phenylalanine amide (6).

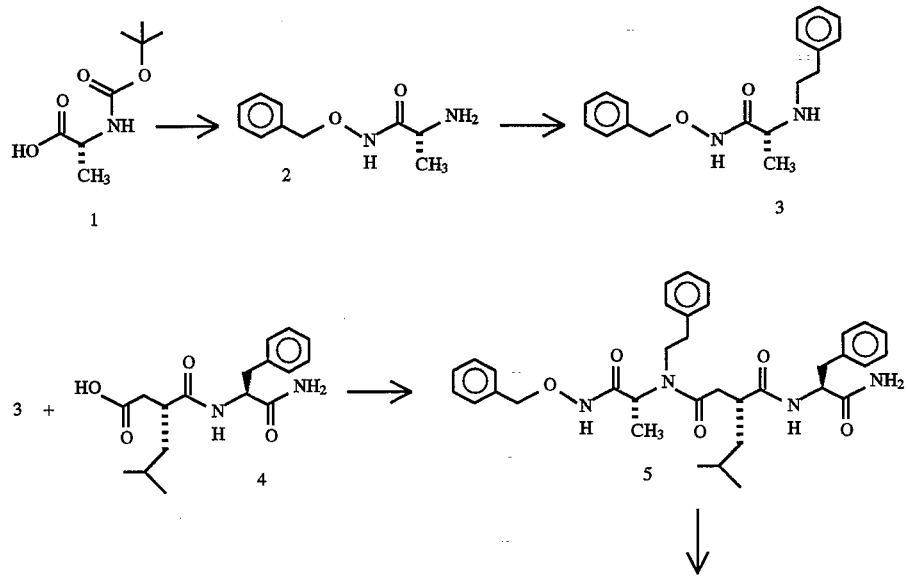

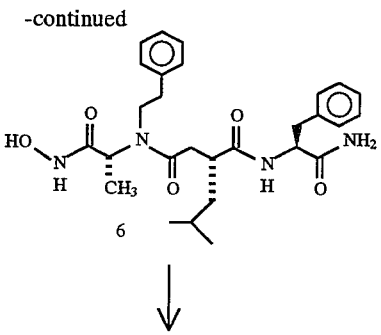

A mixture of 1.70 g (9.0 mmol) of N-t-BOC-D-alanine, 1, 1.35 g (10.0 mmol) of 1-hydroxybenzotriazole, 1.27 mL of 4-ethylmorpholine (10.0 mmol), and 2.00 g (12.5 mmol) of O-benzylhydroxylamine hydrochloride are stirred in 20 mL of DMF at room temperature under an inert atmosphere as 1.92 g (10.0 mmol) of 1-(3-dimethylaminopropyl)-3-ethylcarbodiimide hydrochloride is added. The mixture is stirred for 24 h and concentrated under reduced pressure. The residue is taken up in ethyl acetate plus dichloromethane and the organic solution is extracted twice with cold 1M hydrochloric acid solution, twice with cold 1M sodium hydroxide solution, once with water, and once with brine. The organic layer is dried over sodium sulfate, filtered, and concentrated under reduced pressure. This residue is dissolved in 30 mL of 5M HCl in ethyl acetate, stirred for 5 h, then concentrated under reduced pressure to provide 2 as its hydrochloride salt. This material is dissolved in 15 mL of methanol along with 2.40 g (20.0 mmol) of phenylacetaldehyde and cooled in an ice bath. Sodium cyanoborohydride (2.00 g, 31.8 mmol) is added to the mixture and after 2 h the cold bath is removed. After stirring an additional 20 h the mixture is concentrated under reduced pressure, and the residue is partitioned between water and ethyl acetate. The organic layer is dried over sodium sulfate, filtered, and concentrated under reduced pressure to provide a residue which is purified by column chromatography (silica gel) eluting with dichloromethane/methanol mixtures to give 3.

A mixture of 0.250 g (0.838 mmol) of 3, 0.135 g (1.00 mmol) of 1-hydroxybenzotriazole, 0.127 mL (1.0 mmol) of 4-ethylmorpholine, and 0.320 g (1.00 mmol) of 4 (prepared in the same manner as Compound 6 in Example 1) are stirred in 2 mL of DMF at room temperature under an inert atmosphere as 0.192 g (1.00 mmol) of 1-(3-dimethylaminopropyl)-3-ethylcarbodiimide hydrochloride is added. The mixture is stirred for 24 h and concentrated under reduced pressure. The residue is taken up in ethyl acetate plus dichloromethane and the organic solution is extracted twice with 1M hydrochloric acid solution, twice with 1M sodium hydroxide solution, once with water, and once with brine. The organic layer is dried over sodium sulfate, filtered, and concentrated under reduced pressure to provide a residue which is purified by column chromatography (silica gel) eluting with dichloromethane/isopropanol mixtures to give 5.

A solution of 0.120 g (0.276 mmol) of 5 in 5 mL of methanol is subjected to hydrogenolysis using 0.040 g of 10% palladium on carbon under one atmosphere of hydrogen. The catalyst is removed by filtration and 6 is isolated after concentration under reduced pressure.

EXAMPLE 5

Synthesis of trans-1-(R)-{N-[1-(R)-(N-Hydroxyaminocarbonyl)ethyl]-N-(2-phenylethyl) aminocarbonyl }-2-(R)-{N-(2-phenylethyl) aminocarbonyl }cyclohexane (5), and trans-1-(S)-{N-[1-(R)-(N-hydroxyaminocarbonyl)ethyl]-N-(2-phenylethyl)aminocarbonyl-2-(S)-{N-(2-phenylethyl)aminocarbonyl}cyclohexane (6)

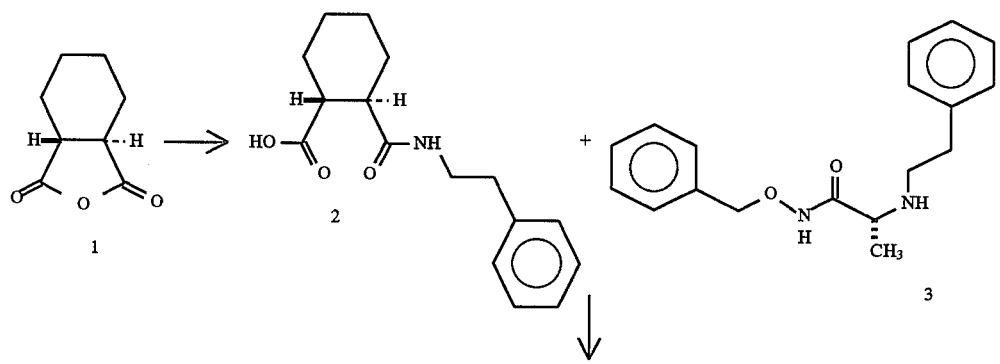

-continued

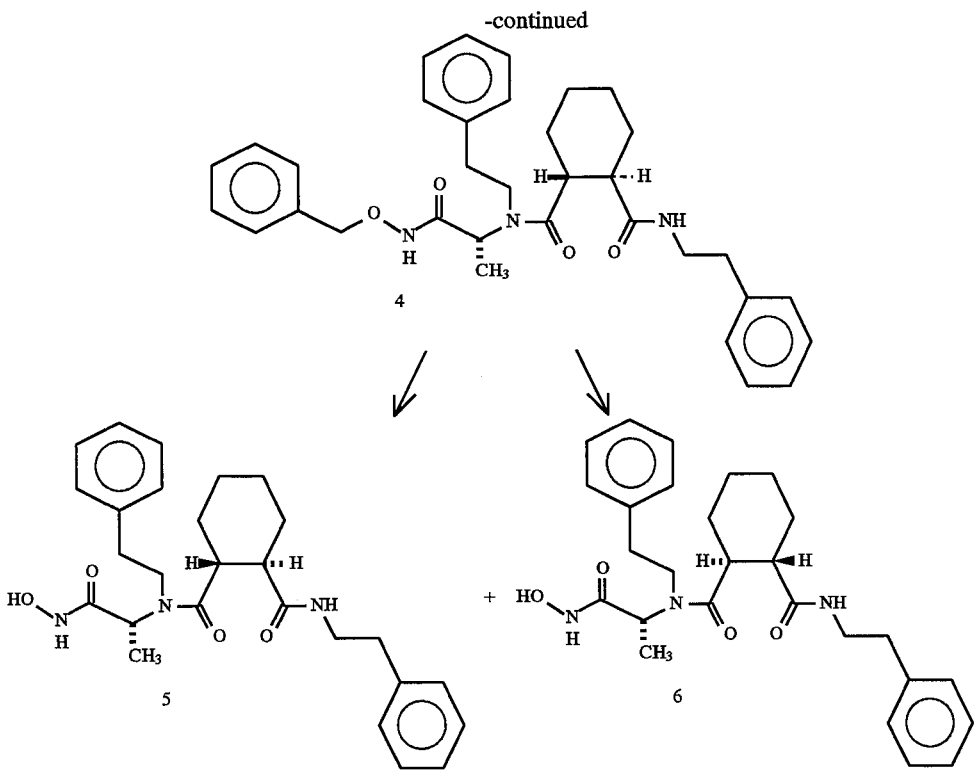

A mixture of 20.0 g (0.130 mol) of trans- 1,2-cyclohexanedicarboxylic anhydride, 1, in 120 mL of DMF at room temperature under an inert atmosphere is stirred while 30.0 g (0.248 mol) of phenethylamine is added. The mixture is stirred for 24 h and concentrated under reduced pressure. The residue is taken up in ethyl acetate plus dichloromethane and the organic solution is extracted twice with 1M hydrochloric acid solution, once with water, and once with brine. The organic layer is dried over sodium sulfate, filtered, and concentrated under reduced pressure to give 2 as a mixture of diastereomers.

A mixture of 1.25 g (4.54 mmol) of 2, 0.676 g (5.00 mmol) of 1-hydroxybenzotriazole, 0.635 mL (5.0 mmol) of 4-ethylmorpholine, and 1.49 g (5.00 mmol) of 3 (made in the same manner as Compound 3 in Example 4) are stirred in 10 mL of DMF at room temperature under an inert atmosphere as 0.958 g (5.00 mmol) of 1-(3-dimethylaminopropyl)-3-ethylcarbodiimide hydrochloride is added. The mixture is stirred for 24 h and concentrated under reduced pressure. The residue is taken up in ethyl acetate plus dichloromethane and the organic solution is extracted twice with 1M hydrochloric acid solution, twice with cold 1M sodium hydroxide solution, once with water, and once with brine. The organic layer is dried over sodium sulfate, filtered, and concentrated under reduced pressure to provide a residue which is purified by column chromatography (silica gel) eluting with dichloromethane/isopropanol mixtures to give 4.

A solution of 0.120 g (0.216 mmol) of 4 in 5 mL of methanol is subjected to hydrogenolysis using 0.040 g of 10% palladium on carbon under one atmosphere of hydrogen. The catalyst is removed by filtration and concentrated under reduced pressure. Purification by preparative reversed-phased high performance liquid chromatography with mixtures of water, acetonitrile, and trifluoroacetic acid provides 5 and 6.

EXAMPLE 6

Synthesis of 2-(R)-{{N-[1-(R)-(N-Hydroxyaminocarbonyl)-3-phenylpropyl]-N-decylaminocarbonyl}methyl}cyclohexanone (6) and 2-(S)-{{N-[1-(R)-(N-Hydroxyaminocarbonyl)-3-phenylpropyl]-N-decylaminocarbonyl}methyl}cyclohexanone(7).

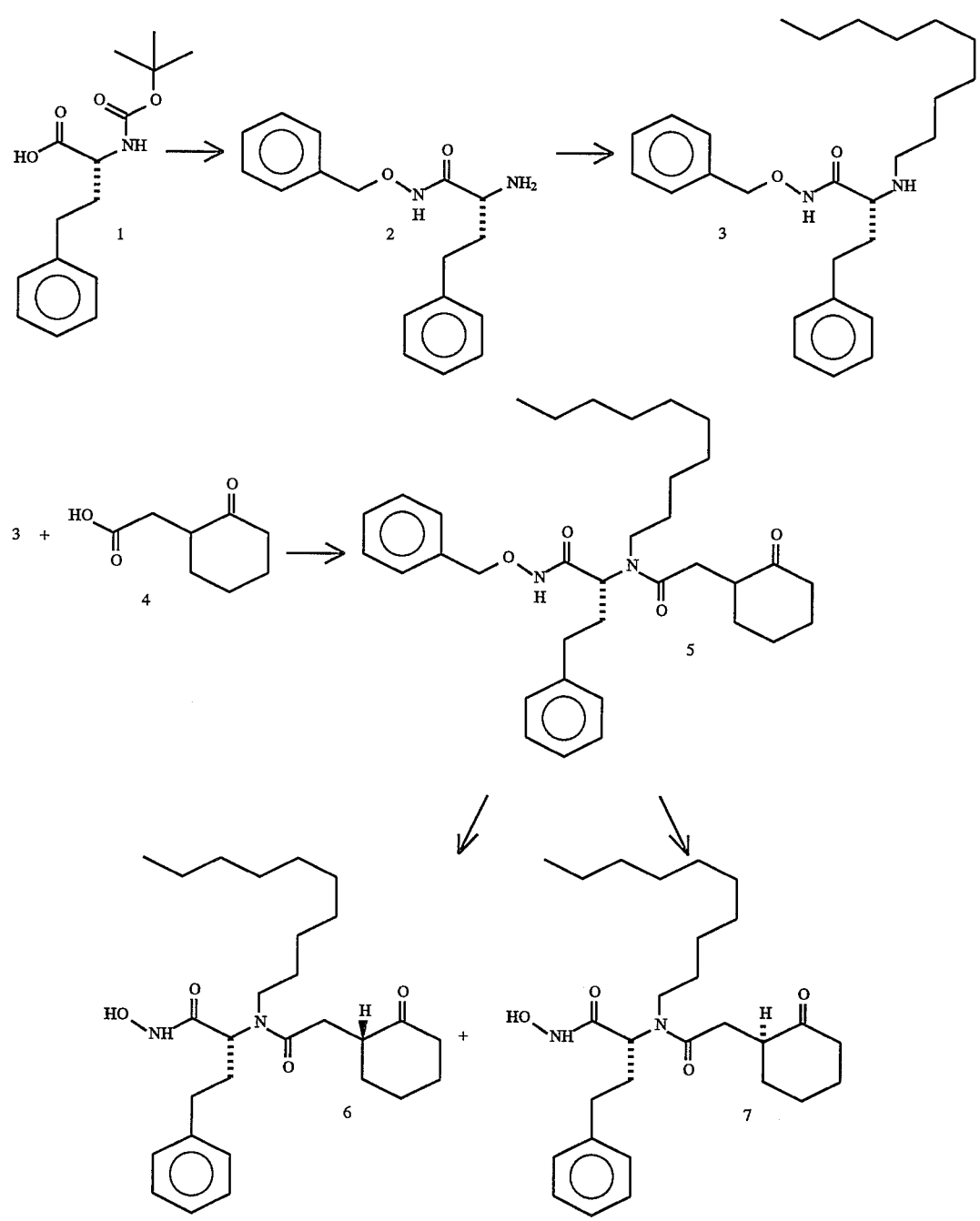

A mixture of 2.51 g (9.0 mmol) of N-t-BOC-D-homophenylalanine, 1, 1.35 g (10.0 mmol) of 1-hydroxybenzotriazole, 1.27 mL of 4-ethylmorpholine (10.0 mmol), and 2.00 g (12.5 mmol) of O-benzylhydroxylamine hydrochloride are stirred in 20 mL of DMF at room temperature under an inert atmosphere as 1.92 g (10.0 mmol) of 1-(3-dimethylaminopropyl)-3-ethylcarbodiimide hydrochloride is added. The mixture is stirred for 24 h and concentrated under reduced pressure. The residue is taken up in ethyl acetate plus dichloromethane and the organic solution is extracted twice with cold 1M hydrochloric acid solution, twice with cold 1M sodium hydroxide solution, once with water, and once with brine. The organic layer is dried over sodium sulfate, filtered, and concentrated under reduced pressure. The resulting residue is dissolved in 30 mL of 5M HCl in ethyl acetate, stirred for 5 h, then concentrated under reduced pressure to provide 2 as its hydrochloride salt. This material is dissolved in 15 mL of methanol along with 3.12 g (20.0 mmol) of decyl aldehyde and cooled in an ice bath. Sodium cyanoborohydride (2.00 g, 31.8 mmol) is added to the mixture and after 2 h the cold bath is removed. After stirring an additional 20 h the mixture is concentrated under reduced pressure, and the residue is partitioned between water and ethyl acetate. The organic layer is dried over sodium sulfate, filtered, and concentrated under reduced pressure to provide a residue which is purified by column chromatography (silica gel) eluting with dichloromethane/methanol mixtures to give 3.

A mixture of 0.400 g (0.942 mmol) of 3, 0.135 g (1.00 mmol of 1-hydroxybenzotriazole, 0.127 mL (1.0 mmol) of 4-ethylmorpholine, and 0.156 g (1.00 mmol) of 4 are stirred in 2 mL of DMF at room temperature under an inert atmosphere as 0.192 g ( 1.00 mmol) of 1-(3-dimethylaminopropyl)-3 -ethylcarbodiimide hydrochloride is added. The mixture is stirred for 24 h and concentrated under reduced pressure. The residue is taken up in ethyl acetate plus dichloromethane and the organic solution is extracted twice with 1M hydrochloric acid solution, twice with 1M sodium hydroxide solution, once with water, and once with brine. The organic layer is dried over sodium sulfate, filtered, and concentrated under reduced pressure to provide a residue which is purified by column chromatography (silica gel) eluting with dichloromethane/isopropanol mixtures to give 5.

A solution of 0.125 g (0.222 mmol) of 5 in 5 mL of methanol is subjected to hydrogenolysis using 0.050 g of 10% palladium on carbon under one atmosphere of hydrogen. The catalyst is removed by filtration and the mixture is concentrated under reduced pressure. Purification by preparative reversed-phased high performance liquid chromatography with mixtures of water, acetonitrile, and trifluoroacetic acid provides 6 and 7.

EXAMPLE A

A tablet composition for oral administration, according to the present invention, is made comprising:

| Component | Amount |
|---|---|
| 3-{N-[(N-Hydroxyaminocarbonyl)methyl]-N-decylaminocarbonyl}-2-(R)-isobutylpropanoyl-L-phenylalanine amide[2] | 15. mg |
| Lactose | 120. mg |
| Maize Starch | 70. mg |
| Talc | 4. mg |
| Magnesium Stearate | 1. mg |

[2]:a hydroxamic acid prepared according to Example 2. Other compounds having a structure according to Formula I are used with substantially similar results.

EXAMPLE B

A capsule for oral administration, according to the present invention, is made comprising:

| Component | Amount (% w/w) |
|---|---|
| 3-{N-[1-(R)-(N-Hydroxyaminocarbonyl)ethyl]-N-(2-phenylethyl)aminocarbonyl}-2-(R)-isobutylpropanoyl-L-phenylalanine amide | 15% |
| Polyethylene glycol | 85% |

[3]:a hydroxamic acid prepared according to Example 3. Other compounds having a structure according to Formula I are used with substantially similar results.

What is claimed is:
1. A compound having a structure according to Formula I

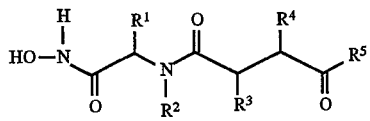

wherein
(A)
(1) $R^1$ is hydrogen; alkyl; heteroalkyl; alkenyl; benzyl, a carbocyclic ring; alkoxy; carbocycle-alkyl; carbocycle-heteroalkyl; or carbocycle-thio;
(2) $R^2$ is hydrogen; alkyl; alkenyl; alkynyl; a carbocyclic ring; carbocycle-alkyl; or carbocycle-heteroalkyl;
(3) $R^3$ is hydrogen or alkyl;
(4) $R^4$ is alkyl; heteroalkyl; alkylamino; acylamino; carboxyalkyl; aminoalkyl; a carbocyclic ring; or a moiety capable of bearing a charge: and
(5) $R^5$ is
(a) $-N(R^9)CH(R^{10})(R^{11})$ where
(i) $R^9$ is hydrogen or alkyl; and
(ii) $R^{10}$ and $R^{11}$ are, independently, hydrogen, alkyl, arylalkyl alkoxyacyl, or aminoacyl; or
(iii) $R^9$ and $R^{10}$ together with the nitrogen and carbon atoms to which they are bonded comprise a 4–9 atom monocyclic heterocyclic ring; or
(b) an amino acid or a peptide having 2 or 3 amino acids, wherein said amino acid or ,said peptide is bonded to Formula (I) via its amino group;
(B) and ,where $R^4$ and $R^5$ may together comprise a 3–13 atom monocyclic carbocyclic ring, or a 7–17 atom polycyclic carbocyclic ring;
or a pharmaceutically-acceptable salt biohydrolyzable amide or biohydrolyzable ester thereof.
2. The compound of claim 1, wherein $R^3$ is hydrogen.
3. The compound of claim 1, wherein $R^2$ is alkyl, alkenyl, alkynyl, carbocycle-alkyl, heterocycle-alkyl, or carbocycle-heteroalkyl.
4. The compound of claim 3, wherein $R^2$ is $C_4$–$C_{10}$ alkyl, $C_4$–$C_{10}$ alkenyl, or carbocycle-alkyl.
5. The compound of claim 4, wherein $R^2$ is n-decyl, 2-methylpropyl, 2-phenylethyl, or 3-phenylpropyl.
6. The compound of claim 3, wherein $R^4$ is alkyl, heteroalkyl, or aminoalkyl.
7. The compound of claim 6, wherein $R^4$ is 2-methylpropyl or 4-aminobutyl.
8. The compound of claim 3, wherein $R^5$ is $-N(R^9)CH(R^{10})(R^{11})$, where $R^9$ is hydrogen; and $R^{10}$ and $R^{11}$ are, independently, hydrogen, alkyl, arylalkyl, alkoxyacyl, or aminoacyl.
9. The compound of claim 8, wherein $R^{10}$ is hydrogen or arylalkyl.
10. The compound of claim 9, wherein $R^{10}$ is hydrogen and $R^{11}$ is benzyl or aminoacyl.
11. The compound of claim 9, wherein $R^{10}$ is arylalkyl and $R^{11}$ is aminoacyl.
12. A pharmaceutical composition comprising:
(a) a safe and effective amount of compound of claim 1; and
(b) a pharmaceutically-acceptable carrier.
13. A compound having a structure according to Formula I

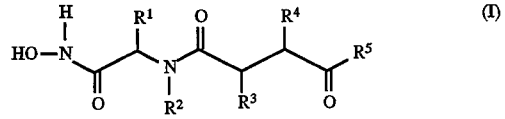

wherein
(A)
(1) $R^1$ is hydrogen; alkyl; benzyl; or carbocycle-alkyl;
(2) $R^2$ is alkyl; alkenyl; carbocycle-alkyl; heterocycle-alkyl; or carbocycle-heteroalkyl;

(3) $R^3$ is hydrogen; or alkyl;

(4) $R^4$ is alkyl; heteroalkyl; or aminoalkyl; and (5) $R^5$ is (a) —N($R^9$)CH($R^{10}$)($R^{11}$), where (i) $R^9$ is hydrogen; and (ii) $R^{10}$ and $R^{11}$ are, independently, hydrogen, alkyl, arylalkyl, alkoxyacyl, or aminoacyl; or (iii) $R^9$ and $R^{10}$, together with the nitrogen and carbon atoms to which they are bonded, comprise a 4–9 atom monocyclic heterocyclic ring; or (b) an amino acid or a peptide having 2 or 3 amino acids, wherein said amino acid or said peptide is bonded to Formula (I) via its amino group;

(B) and where (1) $R^3$ and $R^4$ may together comprise a 3–9 atom monocyclic carbocyclic ring; or (2) $R^4$ and $R^5$ may together comprise a 3–13 atom monocyclic carbocyclic ring; a 7–17 atom polycyclic carbocyclic ring; a 4–9 atom monocyclic heterocyclic ring; or a 7–17 atom polycyclic heterocyclic ring;

or a pharmaceutically-acceptable salt, biohydrolyzable amide or biohydrolyzable ester thereof.

14. A compound selected from the group consisting of:

3-{N-[(N-Hydroxyaminocarbonyl)methyl]-N-isobutylaminocarbonyl}-2-(R)-isobutylpropanoyl-L-phenylalanine amide;

3-{N-[(N-Hydroxyaminocarbonyl)methyl]-N-decylaminocarbonyl }-2-(R)-isobutylpropanoyl-L-phenylalanine amide;

3-{N-[(N-Hydroxyaminocarbonyl)methyl]-N-decylaminocarbonyl}-2-(R)-isobutylpropanoic acid, 2-phenylethyl amide;

3-{N-[1-(R)-(N-Hydroxyaminocarbonyl)ethyl]-N-(2-phenylethyl)-aminocarbonyl}-2-(R)-isobutylpropanoyl-L-phenylalanine amide;

trans- 1-(R)-{N-[1-(R)-(N-Hydroxyaminocarbonyl)ethyl]-N-(2-phenylethyl)aminocarbonyl}-2-(R)-{N-(2-phenylethyl)aminocarbonyl}cyclohexane;

trans- 1-(S)-(N-[1-(R)-(N-hydroxyaminocarbonyl)ethyl]-N-(2-phenylethyl)aminocarbonyl-2-(S)-{N-(2-phenylethyl)aminocarbonyl }cyclohexane;

2-(R)-{{N-[1-(R)-(N-Hydroxyaminocarbonyl)-3-phenylpropyl]-N-decylaminocarbonyl}methyl}cyclohexanone; and 2-(S)-{{N-[1 -(R)-(N-Hydroxyaminocarbonyl)-3-phenylpropyl]-N-decylaminocarbonyl}methyl}cyclohexanone.

15. A pharmaceutical composition comprising:

(a) a safe and effective mount of a compound of claim 6; and (b) a pharmaceutically-acceptable carrier.

16. The compound of claim 1, wherein $R^4$ and $R^5$ together comprise a 3–13 atom monocyclic carbocycle ring or a 7–17 atom polycyclic carbocyclic ring.

\* \* \* \* \*